United States Patent [19]
Panescu et al.

[11] Patent Number: 5,769,847
[45] Date of Patent: Jun. 23, 1998

[54] SYSTEMS AND METHODS FOR CONTROLLING TISSUE ABLATION USING MULTIPLE TEMPERATURE SENSING ELEMENTS

[75] Inventors: Dorin Nmi Panescu, Sunnyvale; James G. Whayne, Saratoga; Sidney D. Fleischman, Menlo Park; David K. Swanson, Mountain View, all of Calif.

[73] Assignee: EP Technologies, Inc., San Jose, Calif.

[21] Appl. No.: 638,989

[22] Filed: Apr. 24, 1996

Related U.S. Application Data

[63] Continuation of Ser. No. 286,930, Aug. 8, 1994, abandoned, which is a continuation-in-part of Ser. No. 266,934, Jun. 27, 1994, abandoned.

[51] Int. Cl.⁶ .................................................. A61B 17/36
[52] U.S. Cl. ............................... 606/42; 606/48; 606/31; 607/101
[58] Field of Search .......................... 606/27–32, 37–42, 606/45–52; 607/100–102; 128/642

[56] References Cited

U.S. PATENT DOCUMENTS

| | | |
|---|---|---|
| 4,411,266 | 10/1983 | Cosman . |
| 4,413,633 | 11/1983 | Yanda . |
| 4,565,200 | 1/1986 | Cosman . |
| 4,681,122 | 7/1987 | Winters et al. . |
| 4,860,744 | 8/1989 | Johnson et al. ............................ 606/31 |
| 4,907,589 | 3/1990 | Cosman . |
| 4,935,345 | 6/1990 | Guilbeau et al. . |
| 4,960,109 | 10/1990 | Lele . |
| 4,966,597 | 10/1990 | Cosman ..................................... 606/50 |
| 4,998,933 | 3/1991 | Eggers et al. ............................. 606/31 |
| 5,057,105 | 10/1991 | Malone et al. . |
| 5,122,137 | 6/1992 | Lennox . |
| 5,156,151 | 10/1992 | Imran ....................................... 607/122 |
| 5,178,620 | 1/1993 | Eggers et al. . |
| 5,191,883 | 3/1993 | Lennox et al. . |
| 5,249,585 | 10/1993 | Turner et al. . |
| 5,277,201 | 1/1994 | Stern . |
| 5,383,917 | 1/1995 | Desai et al. . |
| 5,391,199 | 2/1995 | Ben-Haim . |
| 5,423,808 | 6/1995 | Edwards et al. . |
| 5,496,312 | 3/1996 | Klicek . |

FOREIGN PATENT DOCUMENTS

| | | |
|---|---|---|
| 3838840 A1 | 5/1990 | Germany . |
| WO 93/20770 | 10/1993 | WIPO . |

*Primary Examiner*—Michael Peffley
*Attorney, Agent, or Firm*—Oppenheimer Poms Smith

[57] ABSTRACT

A system and associated method ablate body tissue using multiple emitters of ablating energy. The system and method convey ablating energy individually to each emitter in a sequence of power pulses. The system and method periodically sense temperature at each emitter and compare the sensed temperatures to a desired temperature established for all emitters to generate a signal individually for each emitter based upon the comparison. The system and method individually vary the power pulse to each emitter based upon the signal for that emitter to maintain the temperatures at all emitters essentially at the desired temperature during tissue ablation.

68 Claims, 16 Drawing Sheets

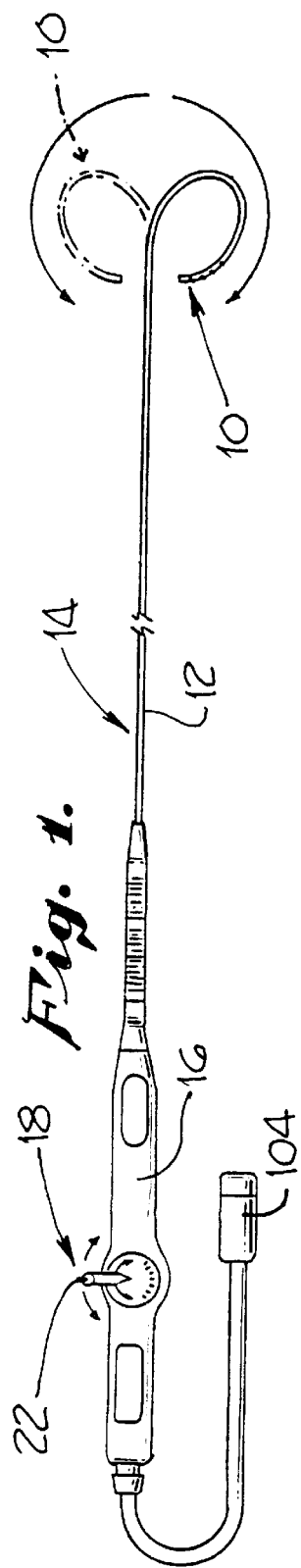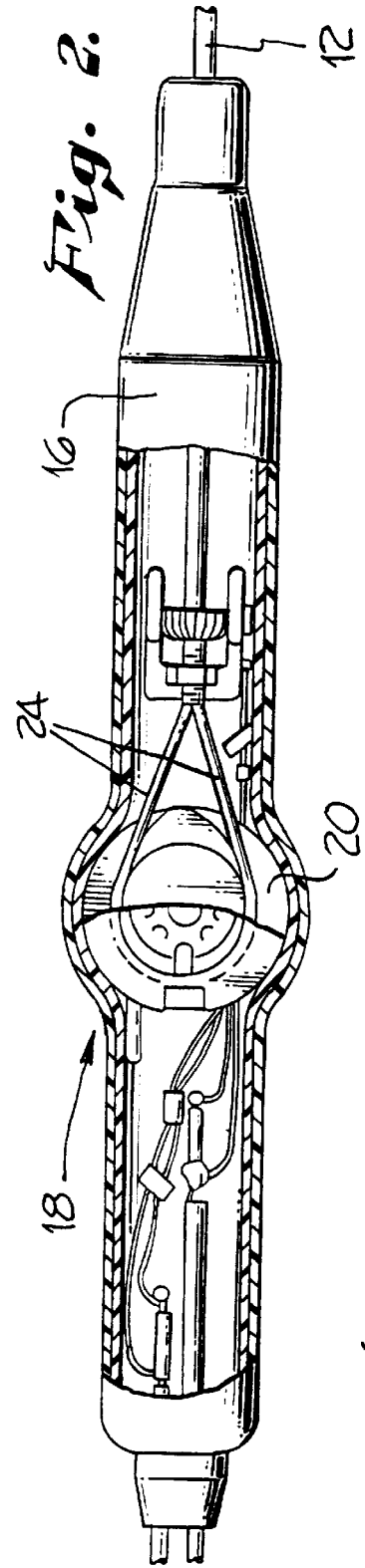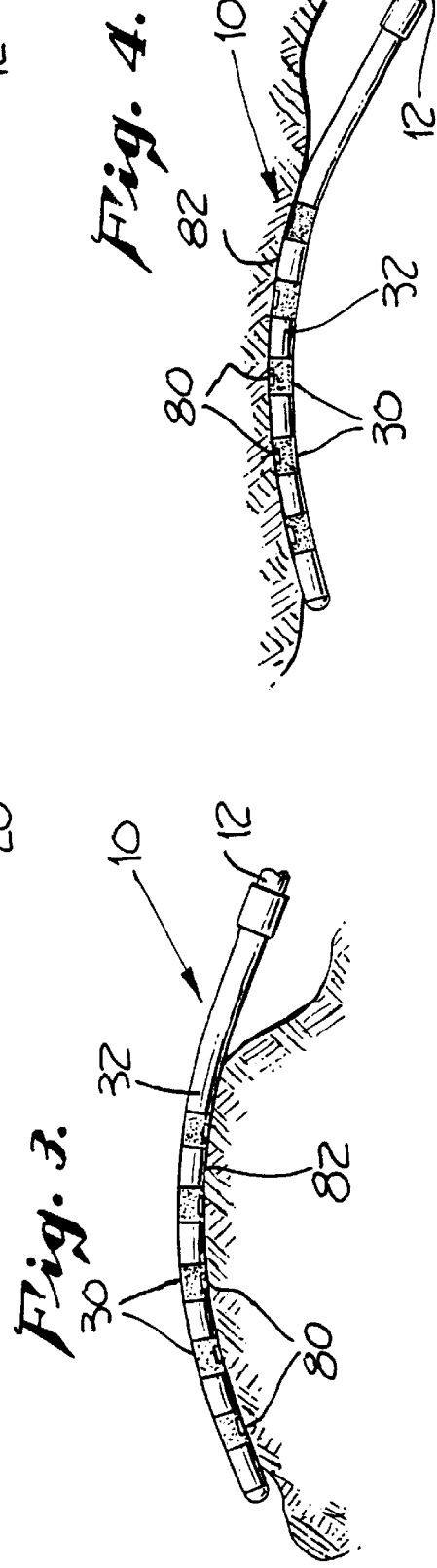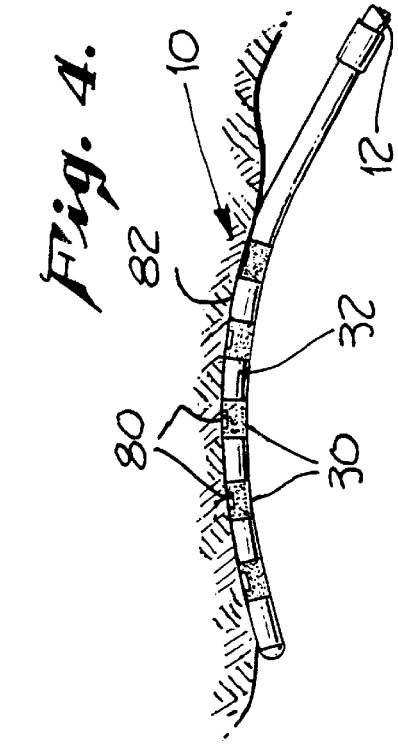

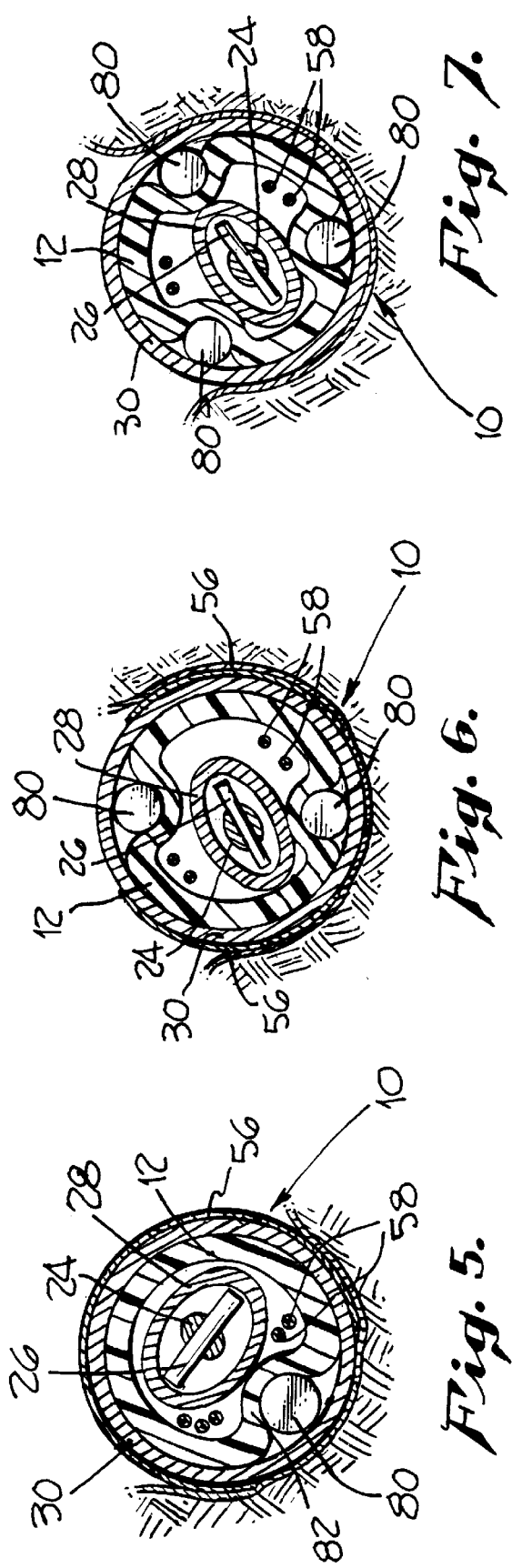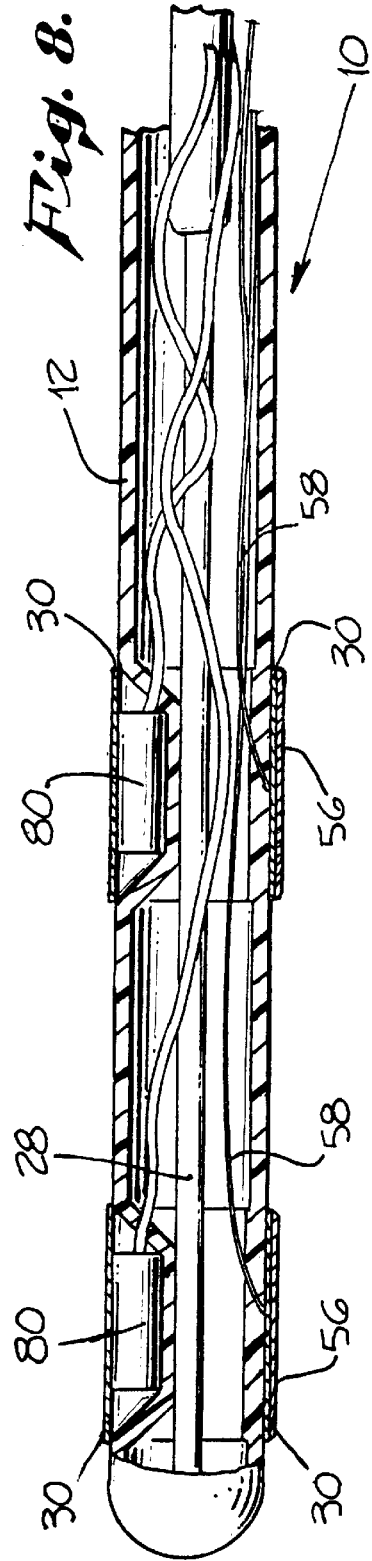

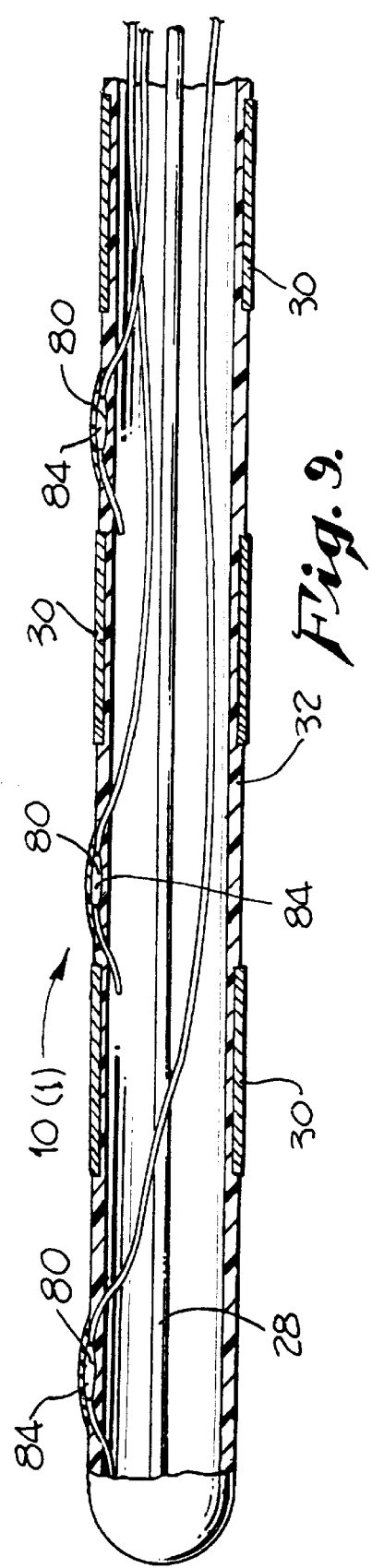
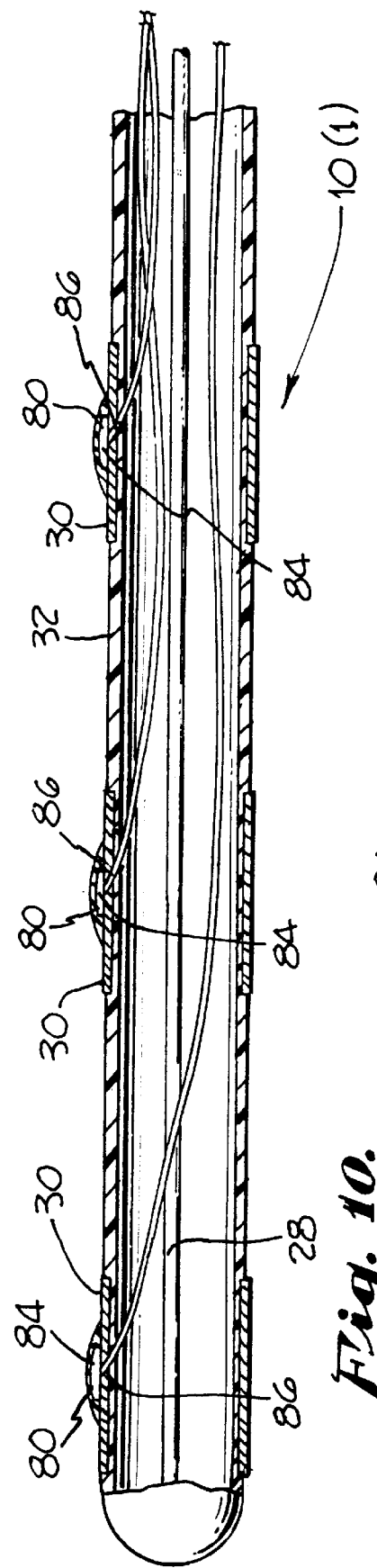
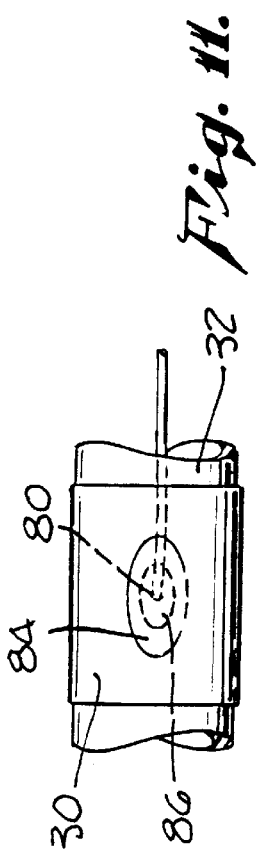

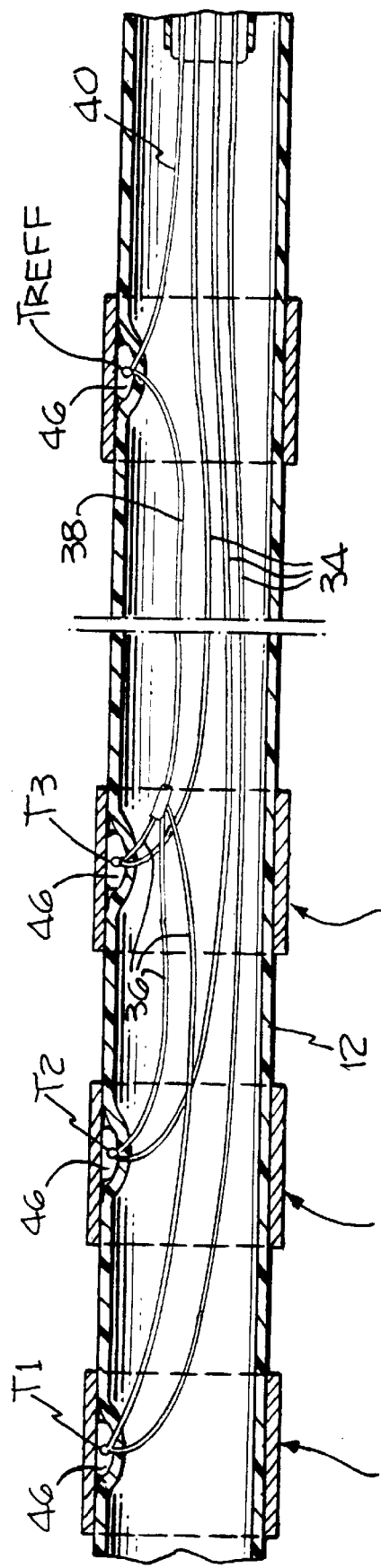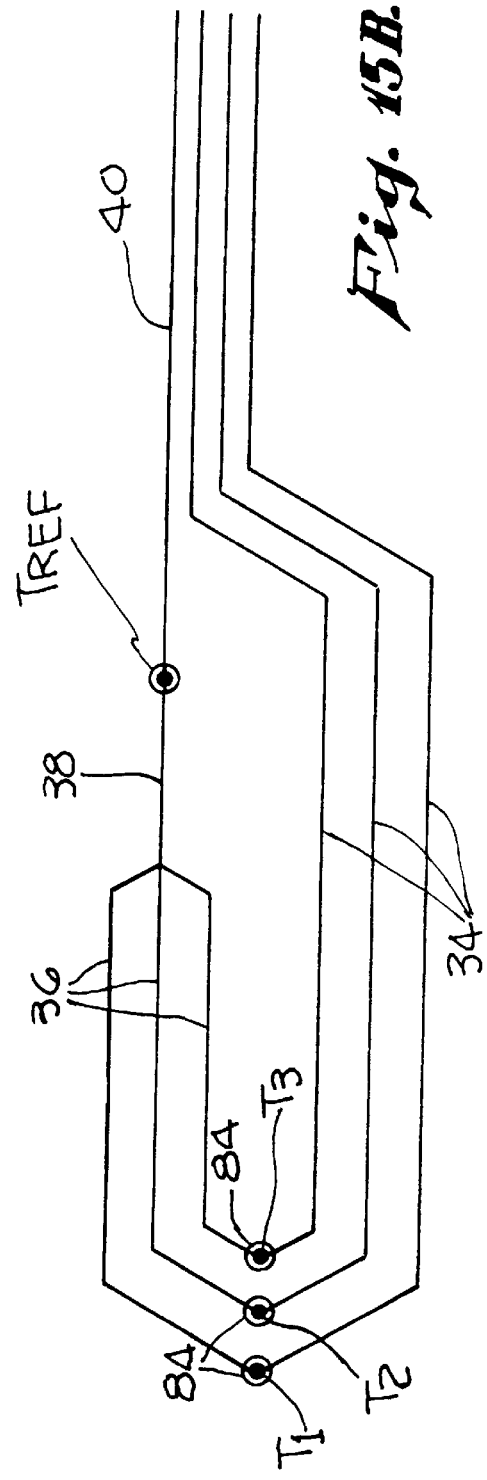

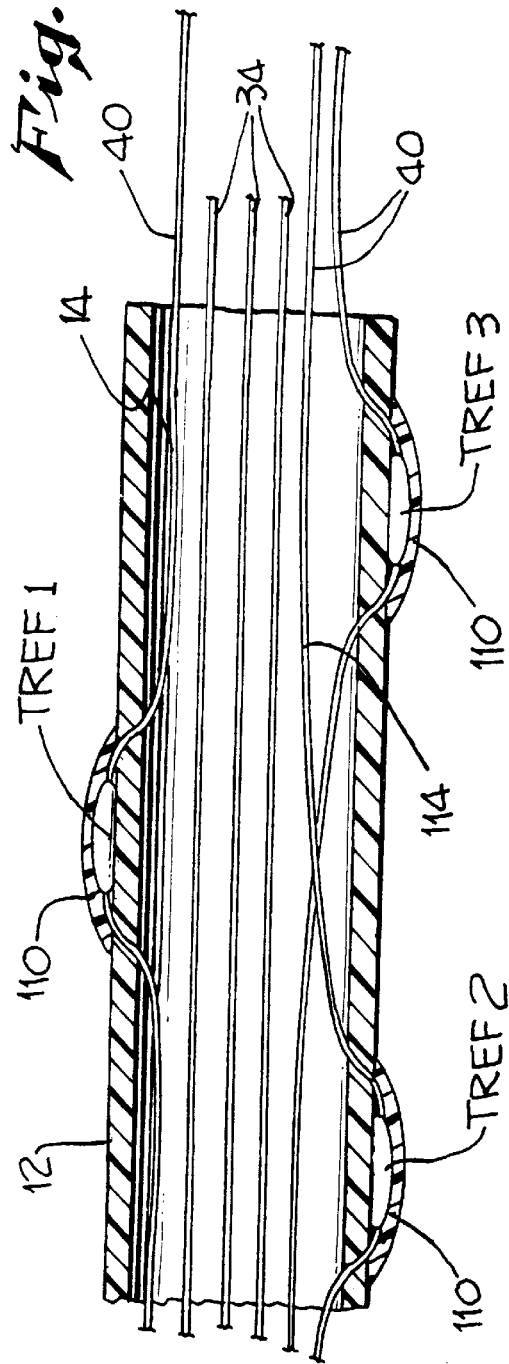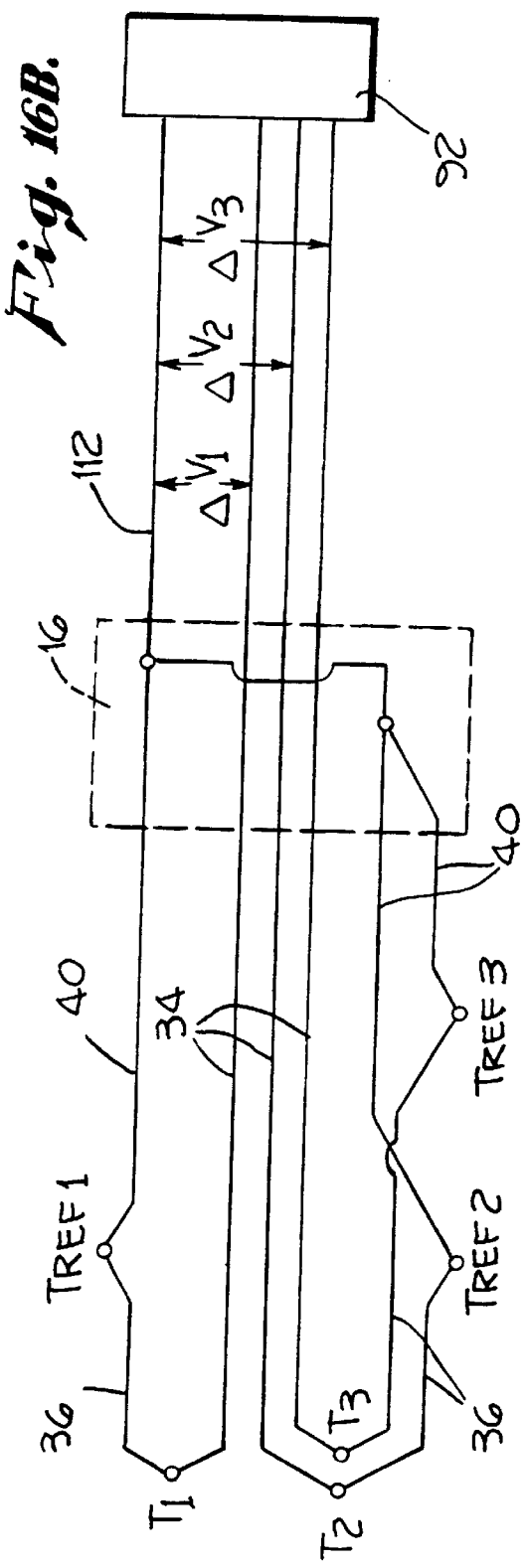

INDIVIDUAL AMPLITUDES
COLLECTIVE DUTY CYCLE

Fig. 22. COLLECTIVE AMPLITUDE INDIVIDUAL DUTY CYCLES

TEMPERATURE CONTROL WITH HYSTERESIS

DIFFERENTIAL TEMPERATURE DISABLING

SYSTEMS AND METHODS FOR CONTROLLING TISSUE ABLATION USING MULTIPLE TEMPERATURE SENSING ELEMENTS

This is a continuation of application Ser. No. 08/286,930 filed on Aug. 8, 1994 (now abandoned); which is a c-i-p of application Ser. No. 08/266,934 filed on Jun. 27, 1994 (now abandoned).

FIELD OF THE INVENTION

The invention relates to systems and methods for ablating myocardial tissue for the treatment of cardiac conditions.

BACKGROUND OF THE INVENTION

Physicians make use of catheters today in medical procedures to gain access into interior regions of the body to ablate targeted tissue areas. It is important for the physician to be able to precisely locate the catheter and control its emission of energy within the body during tissue ablation procedures.

For example, in electrophysiological therapy, ablation is used to treat cardiac rhythm disturbances.

During these procedures, a physician steers a catheter through a main vein or artery into the interior region of the heart that is to be treated. The physician places an ablating element carried on the catheter near the cardiac tissue that is to be ablated. The physician directs energy from the ablating element to ablate the tissue and form a lesion.

In electrophysiological therapy, there is a growing need for ablating elements capable of providing lesions in heart tissue having different geometries.

For example, it is believed the treatment of atrial fibrillation requires the formation of long, thin lesions of different curvilinear shapes in heart tissue. Such long, thin lesion patterns require the deployment within the heart of flexible ablating elements having multiple ablating regions. The formation of these lesions by ablation may provide the same therapeutic benefits that the complex suture patterns the surgical maze procedure presently provides, but without invasive, open heart surgery.

As another example, it is believed that the treatment of atrial flutter and ventricular tachycardia requires the formation of relatively large and deep lesions patterns in heart tissue. Merely providing "bigger" electrodes does not meet this need. Catheters carrying large electrodes are difficult to introduce into the heart and difficult to deploy in intimate contact with heart tissue. However, by distributing the larger ablating mass required for these electrodes among separate, multiple electrodes spaced apart along a flexible body, these difficulties can be overcome.

With larger and/or longer multiple electrode elements comes the demand for more precise control of the ablating process. The delivery of ablating energy must be governed to avoid incidences of tissue damage and coagulum formation. The delivery of ablating energy must also be carefully controlled to assure the formation of uniform and continuous lesions, without hot spots and gaps forming in the ablated tissue.

SUMMARY OF THE INVENTION

A principal objective of the invention is to provide improved systems and methods to ablate tissue using multiple ablating elements.

One aspect of the invention provides a system and associated method for ablating body tissue using multiple emitters of ablating energy. The system and method convey ablating energy individually to each emitter in a sequence of power pulses. Each power pulse has a duty cycle (DUTYCYCLE) and an amplitude (AMPLITUDE), which can be expressed either as current or voltage. The power (POWER) delivered to each emitter for ablating tissue is expressed as follows:

$$POWER \sim AMPLITUDE^2 \times DUTY\ CYCLE$$

The system and method periodically sense temperature at each emitter. The system and method compare the sensed temperatures to a desired temperature established for all emitters to generate a signal individually for each emitter based upon the comparison. The system and method individually vary the power pulse to each emitter based upon the signal generated for that emitter. In this way, the system and method maintain temperatures at all emitters essentially at the desired temperature during tissue ablation.

In one embodiment, the system and method vary the power pulse by individually varying the amplitude of the power pulse based upon the signal for that emitter, while maintaining the duty cycle of the power pulses essentially the same for all emitters. In a preferred implementation of this embodiment, the system and method vary amplitude by varying voltage. In a preferred implementation of this embodiment, the duty cycle is set at 1/N, where N is the number of emitters.

In another embodiment, the system and method vary the power pulse by individually varying the duty cycle of the emitter based upon the signal for that emitter, while maintaining the amplitude of the power pulses essentially the same for all emitters.

In another embodiment, the system and method vary the power pulse by individually varying both the duty cycle and the amplitude of the power pulse for each energy emitter based upon the signal for that emitter.

According to another aspect of the invention, a system and method conveying ablating energy to multiple emitters for ablating tissue, while periodically sensing temperature at each emitter. This aspect of the invention selects one of the sensed temperatures based upon preestablished criteria for comparison to a desired temperature to generate a signal. The system and method control the conveyance of ablating energy to all emitters based upon this selected signal.

In a preferred embodiment of this aspect of the invention, the system and method select the highest one of the sensed temperatures.

According to yet another aspect of the invention, the system and method compare the temperature measured at each emitter to the selected temperature to generate a signal individually for each emitter based upon the comparison. The system and method individually control the conveyance of ablating energy to each emitter based upon the signal generated for that emitter.

In a preferred embodiment of this aspect of the invention, the system and method control the conveyance of ablating energy by individually turning off and turning on an energy emitter based upon the signal for that emitter. In this embodiment, the system and method selects for comparison the lowest one of the sensed temperatures.

Another aspect of the invention provides a system and method for ablating body tissue, which periodically sense at least two temperatures at each emitter. The system and method select the hottest one of the selected temperatures and use this selected hottest temperature for comparison with a desired temperature to generate a signal. The system and method control the conveyance of energy to the emitter based upon the signal.

In one variation of this aspect of the invention, the system and method predict the hottest tissue temperature at each emitter based upon the multiple temperatures sensed at that emitter. The system and method use this predicted hottest tissue temperature for comparison with a desired temperature to generate a signal. The system and method control the conveyance of energy to the emitter based upon the signal.

In a preferred embodiment, the system and method convey ablating energy individually to multiple emitters of ablating energy. The system and method periodically sensing at least two temperatures at each emitter. The system and method either select for each emitter the hottest one of the sensed temperatures or derive for each emitter a prediction of the hottest tissue temperature based upon the sensed temperatures. In this embodiment, the system and method compare either the hottest temperature for each emitter or the predicted hottest tissue temperature for each emitter to a desired temperature established for all emitters to generate a signal individually for each emitter based upon the comparison. The system and method individually control the conveyance of energy to each emitter based upon the signal for that emitter to maintain either the hottest temperature or the predicted hottest tissue temperature at all emitters essentially at the desired temperature during tissue ablation.

The systems and methods that incorporate the various aspects of the invention, either individually or in combination one with another, are well suited for use for catheter-based cardiac ablation.

Other features and advantages of the inventions are set forth in the following Description and Drawings, as well as in the appended Claims.

BRIEF DESCRIPTION OF THE DRAWINGS

FIG. 1 is a view of a probe that carries a flexible ablating element having multiple temperature sensing elements;

FIG. 2 is an enlarged view of the handle of the probe shown in FIG. 1, with portions broken away and in section, showing the steering mechanism for flexing the ablating element;

FIGS. 3 and 4 show the flexure of the ablating element against different tissue surface contours;

FIG. 5 is an end section view of an ablating electrode element carrying one temperature sensing element;

FIG. 6 is an end section view of an ablating electrode element carrying two temperature sensing elements;

FIG. 7 is an end section view of an ablating electrode element carrying three temperature sensing elements;

FIG. 8 is a side section view of a flexible ablating element comprising multiple rigid electrode elements, showing one manner of mounting at least one temperature sensing element beneath the electrode elements;

FIG. 9 is a side section view of a flexible ablating element comprising multiple rigid electrode elements, showing the mounting of at least one temperature sensing element between adjacent electrode elements;

FIG. 10 is a side section view of a flexible ablating element comprising multiple rigid ablating elements, showing the mounting of at least one temperature sensing element on the electrode elements;

FIG. 11 is an enlarged top view of the mounting the temperature sensing element on the rigid electrode shown in FIG. 10;

FIG. 15A is a side section view of the mounting of a star connection as a reference junction for multiple thermocouples;

FIG. 15B is the schematic representation for the star connection of the reference junction for FIG. 15A;

FIG. 16A is a side section view of the mounting of multiple onboard reference thermocouples;

FIG. 16B is a schematic view of the multiple onboard reference thermocouples shown in FIG. 16A;

Figure 12A:
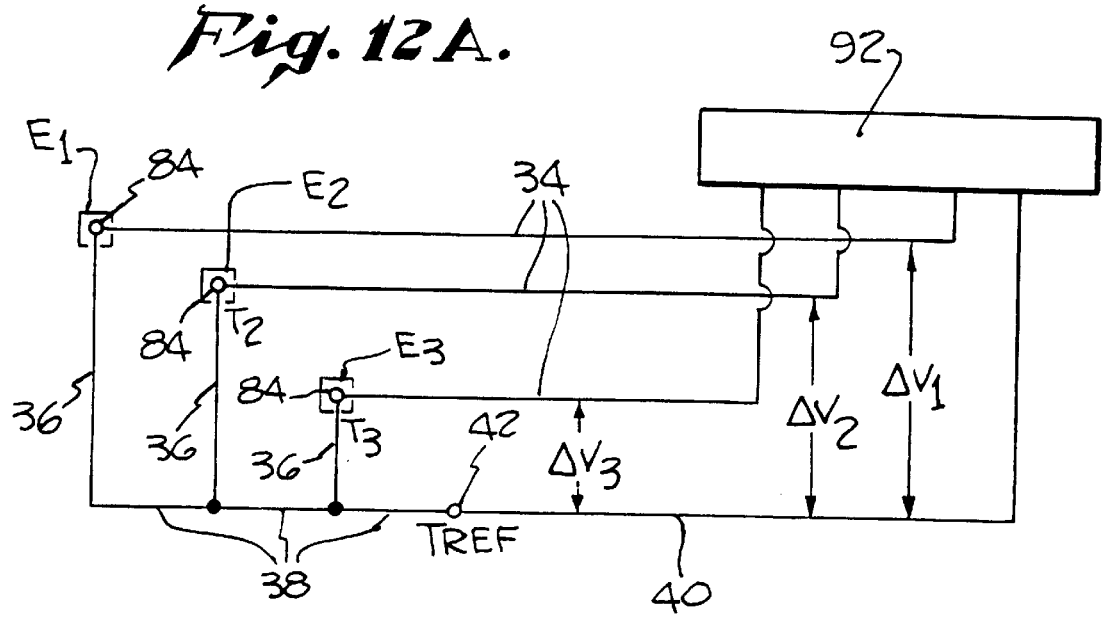
FIGS. 12A/B/C are schematic views of alternative ways of connecting multiple thermocouples for use in association with an ablating element.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

This Specification discloses multiple electrode structures that embody aspects of the invention. This Specification also discloses tissue ablation systems and techniques using multiple temperature sensing elements that embody other aspects of the invention. The illustrated and preferred embodiments discuss these structures, systems, and techniques in the context of catheter-based cardiac ablation. That is because these structures, systems, and techniques are well suited for use in the field of cardiac ablation.

Still, it should be appreciated that the invention is applicable for use in other tissue ablation applications. For example, the various aspects of the invention have application in procedures for ablating tissue in the prostrate, brain, gall bladder, uterus, and other regions of the body, using systems that are not necessarily catheter-based.

I. Flexible Ablating Elements

FIG. 1 shows a flexible ablating element 10 for making lesions within the heart.

The element 10 is carried at the distal end of a catheter body 12 of an ablating probe 14. The ablating probe 14 includes a handle 16 at the proximal end of the catheter body 12. The handle 16 and catheter body 12 carry a steering mechanism 18 for selectively bending or flexing the ablating element 10 in two opposite directions, as the arrows in FIG. 1 show.

The steering mechanism 18 can vary. In the illustrated embodiment (see FIG. 2), the steering mechanism 18 includes a rotating cam wheel 20 with an external steering lever 22 (see FIG. 1). As FIG. 2 shows, the cam wheel 20 holds the proximal ends of right and left steering wires 24. The wires 24 pass through the catheter body 12 and connect to the left and right sides of a resilient bendable wire or spring 26 (best shown in FIGS. 5, 6, and 7) enclosed within a tube 28 inside the ablating element 10.

Further details of this and other types of steering mechanisms for the ablating element 10 are shown in Lundquist and Thompson U.S. Pat. No. 5,254,088, which is incorporated into this Specification by reference.

As FIG. 1 shows, forward movement of the steering lever 22 flexes or curves the ablating element 10 down. Rearward movement of the steering lever 22 flexes or curves the ablating element 10 up.

Various access techniques can be used to introduce the probe 14 into the desired region of the heart. For example, to enter the right atrium, the physician can direct the probe 14 through a conventional vascular introducer through the femoral vein. For entry into the left atrium, the physician can direct the probe 14 through a conventional vascular introducer retrograde through the aortic and mitral valves.

Alternatively, the physician can use the delivery system shown in pending U.S. application Ser. No. 08/033,641, filed Mar. 16, 1993, and entitled "Systems and Methods Using Guide Sheaths for Introducing, Deploying, and Stabilizing Cardiac Mapping and Ablation Probes."

The physician can verify intimate contact between the element 10 and heart tissue using conventional pacing and sensing techniques. Once the physician establishes intimate contact with tissue in the desired heart region, the physician applies ablating energy to the element 10. The type of ablating energy delivered to the element 10 can vary. In the illustrated and preferred embodiment, the element 10 emits electromagnetic radio frequency energy.

The flexible ablating element 10 can be configured in various ways. FIGS. 3 and 4 show one preferred implementation. In this embodiment, the element 10 includes multiple, generally rigid electrode elements 30 arranged in a spaced apart, segmented relationship upon a flexible body 32.

The flexible body 32 is made of a polymeric, electrically nonconductive material, like poly-ethylene or polyurethane.

The segmented electrodes 30 comprise solid rings of conductive material, like platinum. The electrode rings 30 are pressure fitted about the body 32. The flexible portions of the body 32 between the rings 30 comprise electrically nonconductive regions. The segmented electrodes 30 are electrically coupled to wires (not shown) to conduct ablating energy to them.

The body 32 can be flexed between the spaced apart electrodes 30 to bring the electrode 30 into intimate contact along a curvilinear surface of the heart wall, whether the heart surface curves outward (as FIG. 3 shows) or curves inward (as FIG. 4 shows). The number of electrode segments 30 and the spacing between them can vary, according to the particular objectives of the ablating procedure. Likewise, the dimensions of individual electrode segments 30 and underlying body 32 can also vary for the same reason.

Generally speaking, the segmented electrode structure of element 10 is well suited for creating continuous, long and thin lesion patterns, provided that the electrode segments 30 are spaced close enough together and ablating energy is applied simultaneously to adjacent electrode segments 30. Continuous lesion patterns result when adjacent electrode segments are spaced no farther than about 2.5 times the electrode segment diameter apart. However, ablating energy can be selectively applied individually to just one or a selected group of electrode segments, when desired, to further vary the size and characteristics of the lesion pattern.

In the segmented electrode structure of element 10, the diameter of the electrode segments 30 and underlying flexible body 32 can vary from about 4 french to about 10 french. Using rigid electrode segments 30, the minimum diameter is about 1.35 mm.

It has been found that adjacent electrode segments 30 having lengths of less than about 2 mm do not consistently form the desired continuous lesion patterns. Using rigid electrode segments 30, the length of the each electrode segment can vary from about 2 mm to about 10 mm. Using multiple rigid electrode segments longer than about 10 mm each adversely effects the overall flexibility of the element 10(1).

In a representative segmented electrode structure, the flexible body 32 is about 1.35 mm in diameter. The body carries electrode segments 30 each having a length of 3 mm. When eight electrode segments 30 are present and simultaneously activated with 100 watts of radio frequency energy for about 60 seconds, the lesion pattern is long and thin, measuring about 5 cm in length and about 5 mm in width. The depth of the lesion pattern is about 3 mm, which is more than adequate to create the required transmural lesion (the atrial wall thickness is generally less than 3 mm).

The shape of the lesion pattern created by flexible ablating element 10 can be controlled by flexing the body from straight to curvilinear. As already explained, the body can be remotely steered to flex it into a desired shape, or it can possess a fixed memory, preforming it in a desired shape, also from straight to curvilinear.

The flexible ablating element 10 can also be used to form larger and deeper lesion patterns by shaping the support body 32 into a circle or a spiral to increase the density of electrodes per given tissue area. This close diagonal spacing and/or close diametric facing of electrode segments in such structures, coupled with the simultaneous emission of ablating energy by the electrode segments 30 significantly concentrates the distribution of ablating energy. The electrode segments 30 provide an additive heating effect that causes lesions to span across electrode segments that are diagonally close and/or diametrically facing. The spanning lesions create large and deep lesion patterns in the tissue region that the element 10 contacts.

In the illustrated and preferred embodiments, the flexible ablating element 10 carries at least two temperature sensing elements 80. The multiple temperature sensing elements 80 measure temperatures along the length of the element 10.

In this configuration, the sensing elements 80 are preferably located in an aligned relationship along one side of each segmented electrode 30, as FIGS. 3 and 4 show.

The body 32 preferably carries a fluoroscopic marker (like the stripe 82 shown in FIGS. 3 and 4) for orientation purposes. The stripe 82 can be made of a material, like tungsten or barium sulfate, which is extruded into the tubing 12. The extruded stripe can be fully enclosed by the tubing or it can be extruded on the outer diameter of the tubing making it visible to the eye. FIG. 5 shows the marker in the wall of the tubing 12. An alternative embodiment is a fluoro-opaque wire like platinum or gold which can be extruded into the tubing wall. In yet another embodiment, a marker is affixed to the inner diameter of the tubing during manufacturing.

The sensing elements 80 can be on the same side as the fluoroscopic marker 82 (as FIGS. 3 and 4 show), or on the opposite side, as long as the physician is aware of the relative position of them. Aided by the marker 82, the physician orients the element 10(1) so that the temperature sensing elements 80 contact the targeted tissue.

Alternatively, or in combination with the fluoroscopic marker 82, the sensing elements 80 can be consistently located on the inside or outside surface of element 10(1) when flexed in a given direction, up or down. For example, as FIG. 3 shows, when the element 10(1) is flexed downward, the sensing elements 80 are exposed on the inside surface of the element 10(1). As FIG. 4 shows, when the element 10(1) flexed upward, the sensing elements 80 are exposed on the outside surface of the element 10 (1).

Each electrode segment 30 can carry more than a single temperature sensing element 80. As FIGS. 5 to 7 show, each electrode segment 30 can carry one, two, three, or more circumferentially spaced apart temperature sensing elements 80. The presence of multiple temperature sensing elements 80 on a single electrode segment 30 gives the physician greater latitude in positioning the ablating element 10, while still providing temperature monitoring.

As FIG. 5 shows, a thin thermally and electrically insulating coating 56 can be applied to the side of the single sensor-segmented electrode 30 opposite to the temperature sensing element 80, which, in use, is exposed to the blood pool. The coating 56 can be applied, for example, by brushing on a UV-type adhesive or by dipping in polytetrafluoroethylene (PTFE) material.

As FIG. 6 shows, the mask coating 56 lies between the two sensors 80 on the dual-sensor segmented electrode 30. The mask coating 56 minimizes the convective cooling effects of the blood pool upon the regions of the electrode segment 80 that are exposed to it. The temperature condition sensed by the element 80 facing tissue is thereby more accurate. When more than two temperature sensors 80 are used on a given electrode segment 30, masking becomes less advisable, as it reduces the effective surface of the electrode segment 30 available for tissue contact and ablation.

The temperature sensing elements 80 can comprise thermistors or thermocouples.

The sensing element or elements 80 can be attached on or near the segmented electrodes 30 in various way.

For example, as FIG. 8 shows, each sensing element 80 is sandwiched between the exterior of the flexible body 32 and the underside of the associated rigid electrode segment 30. In the illustrated embodiment, the sensing elements 80 comprise thermistors. The body 32 is flexible enough to fit the sensing element 80 beneath the electrode segment 30. The plastic memory of the body 32 maintains sufficient pressure against the temperature sensing element 80 to establish good thermal conductive contact between it and the electrode segment 30.

In an alternative embodiment (as FIG. 9 shows), the temperature sensing element 80 is located between adjacent electrode segments 30. In this arrangement, each sensing element 80 is threaded through the flexible body 32 between adjacent electrode segments 30. In the illustrated embodiment, the temperature sensing elements 80 comprise thermocouples. When the sensing element 80 comprises a thermocouple, an epoxy material 46, such as Master Bond Polymer System EP32HT (Master Bond Inc., Hackensack, N.J.), encapsulates the thermocouple junction 84, securing it to the flexible body 32. Alternatively, the thermocouple junction 84 can be coated in a thin layer of polytetrafluoroethylene (PTFE) material. When used in thicknesses of less than about 0.002 inch, these materials have the sufficient insulating properties to electrically insulate the thermocouple junction 84 from the associated electrode segment 30, while providing sufficient thermally conducting properties to establish thermal conductive contact with electrode segment 30. The use of such materials typically will not be necessary when thermistors are used, because conventional thermistors are already encapsulated in an electrically insulating and thermally conducting material.

Figure 24:
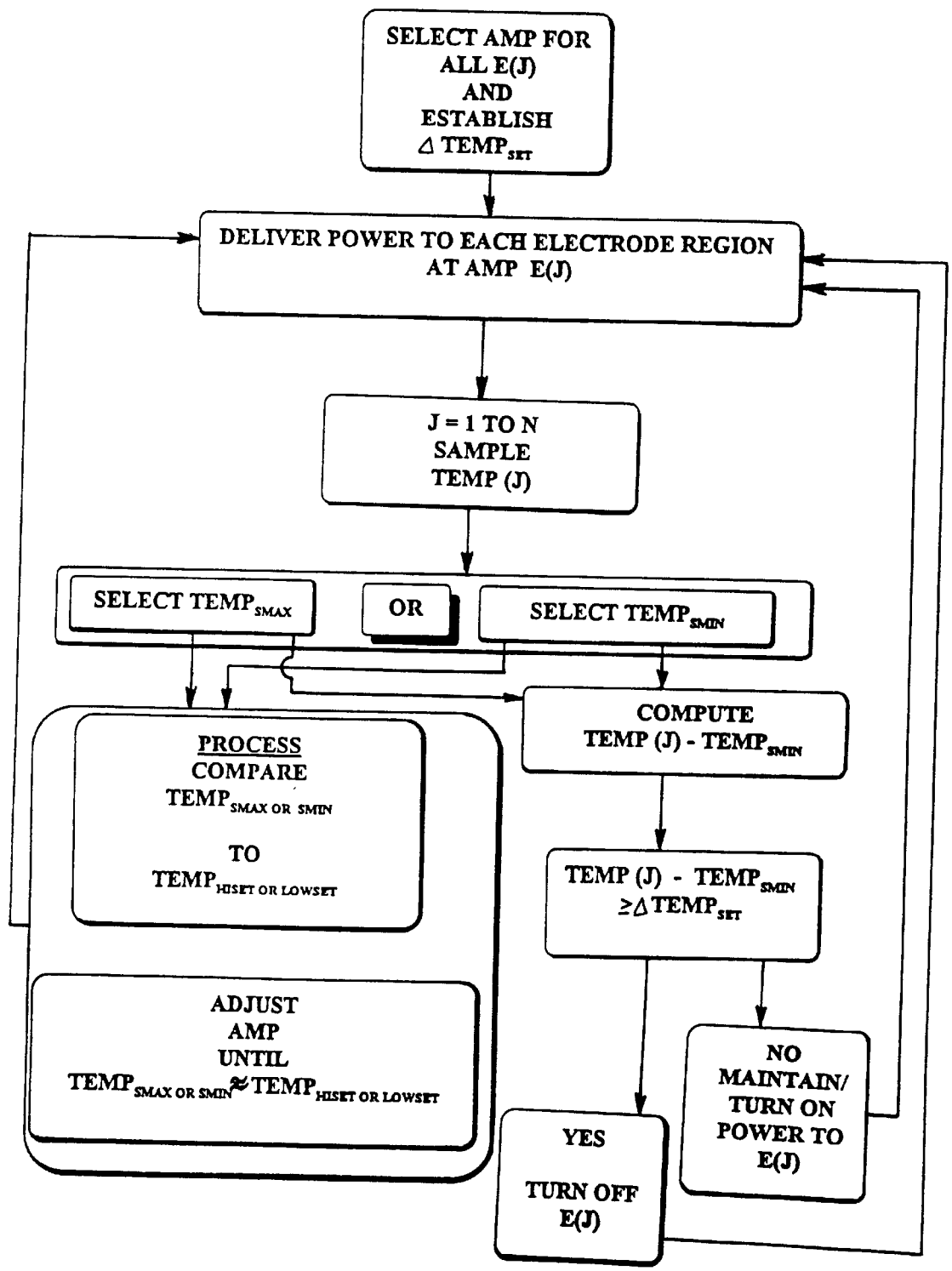
FIG. 24 is a schematic flow chart showing an implementation of the temperature feedback controller shown in FIGS. 19 and 20, using variable amplitude and differential temperature disabling.

In another alternative embodiment (as FIGS. 10 and 11 show), the temperature sensing element 80 physically projects through an opening 86 in each electrode segment 30. As in the embodiment shown in FIG. 24, the sensing elements 80 comprise thermocouples, and a thermally conducting and electrically insulating epoxy material encapsulates the thermocouple junction 84, securing it within the opening 86.

It should be appreciated that some sensing elements 80 can be carried by the electrode segments 30, while other sensing elements 80 can be carried between the element segments 30. Many combinations of sensing element locations are possible, depending upon particular requirements of the ablating procedure.

II. Temperature Sensing Thermocouples For Cardiac Ablation

A. On Board Reference Thermocouple

Each temperature sensing element 80 can comprise a thermistor or a thermocouple. Thermocouples are preferred because, when compared to now-conventional thermistors, a thermocouple is less expensive and presents a smaller, more compact profile. Still, as technology advances, smaller thermistors and other types of miniature temperature sensing elements may become available for use as described in this specification.

Multiple thermocouples can be electrically coupled to sense temperature conditions along an ablating element 10 in various ways. FIGS. 12A; 12B and 12C schematically show three representative embodiments.

In the preferred embodiment shown in FIG. 12A, multiple thermocouples (three of which are shown and designated $T_1$, $_2$, $_3$) are located at or near the ablating electrodes, respectively, E1, E2, and E3. In conventional fashion, each thermocouple $T_{1,2,3}$ includes two electrically insulated wires 34 and 36 of dissimilar metals.

Various types of dissimilar metals can be selected to form the thermocouples $T_{1,2,3}$. For example, nickel-10% chromium can be electrically coupled to either constantan (forming a conventional Type E thermocouple) or nickel-5%(aluminum silicon) (forming a conventional Type K thermocouple); iron can be electrically coupled to constantan (forming a conventional Type J thermocouple); platinum-13% rhodium can be electrically coupled to platinum (forming a conventional Type R thermocouple); platinum-10% rhodium can be electrically couple to platinum (forming a conventional Type S thermocouple); or copper can be electrically coupled to constantan (forming a conventional Type T thermocouple).

In FIG. 12A, the wires 34 are copper and wires 36 are constantan, thereby forming Type T thermocouples. The wires 34 and 36 are electrically insulated, except for the region 84 where they are stripped of insulation and fused together. This region 84 is located at or near the associated electrode E1/E2/E3. This region 84 is encapsulated in an epoxy or PTFE material, as previously described, to electrically insulate the region 84 from the ablating electrode.

Voltage differences measured between the copper wire 34 and the constantan wire 36 of each thermocouple $T_{1, 2, 3}$ varies with the temperature of the junction region 84. The voltage increases or decreases as the temperature of the region 84, respectively, increases or decreases.

As FIG. 12A also shows, a single reference thermocouple $T_{REF}$ is electrically coupled in common to all three thermocouples $T_{1,2,3}$. The reference thermocouple $T_{REF}$ is located in a region where a known temperature condition exists. This aspect will be described in greater detail later.

In FIG. 12A, the reference thermocouple $T_{REF}$ comprises a length of electrically insulated constantan wire 38, locally stripped of insulation and electrically coupled in parallel to the constantan wires 36 of the three thermocouples $T_{1,2,3}$. The reference thermocouple $T_{REF}$ also includes a length of insulated copper wire 40, locally stripped of insulation and electrically coupled to the constantan wire 38.

The junction region of the constantan wire 38 and the copper wire 40 is the thermocouple junction 42 of the reference thermocouple $T_{REF}$. This junction 42 is exposed to a known temperature condition. Like the junction regions 84 between the copper and constantan wires 34 and 36 of the other thermocouples $T_{1,2,3}$ (i.e., the regions 84), this junction region 42 of the reference thermocouple is also encapsulated in an epoxy or PTFE material that electrically insulates it from the ablating electrodes.

An external processing element 92 is electrically coupled to the thermocouples $T_{1,2,3}$ and $T_{REF}$. The particular details of this connection can vary and will be described in greater detail later.

The processing element 92 registers the magnitudes of the voltage differences existing between the copper wire 40 of $T_{REF}$ and the copper wires 34 of each of the thermocouples $T_{1,2,3}$, which are respectively designated $\Delta V_{1,2,3}$ (in FIG. 12A). The processing element 92 derives from the voltage differences $\Delta V_{1,2,3}$ the temperature condition at each thermocouple $T_{1,2,3}$, using the following equation:

$$TEMP_N = TEMP_{REF} + \frac{\Delta V_N}{\alpha}$$

$TEMP_N$ is the temperature condition sensed by a selected thermocouple $T_N$ (where N=1, 2 or 3 in FIG. 12A), the magnitude of which is not known.

$TEMP_{REF}$ is the temperature condition sensed by reference thermocouple $T_{REF}$, the magnitude of which is known.

$\Delta V_N$ is the voltage difference between the copper wire 40 of $T_{REF}$ and the copper wire 34 of the selected thermocouple $T_N$, which is measured and known.

$\alpha$ is a known function (called the Seebeck coefficient), which expresses the relationship between voltage and temperature for the type of dissimilar metals used in the thermocouple.

Further details of this derivation method can be found in a publication available from Omega, entitled *Temperature*, pages T-7 to T-18.

Preferably, the processing element 92 includes a memory chip containing a look up table that inputs $\Delta V_N$ and relates the expression $\Delta V_N/\alpha$ to $TEMP_N$ for the particular thermocouple type used. In this way, the processing element 92 directly converts a measured voltage difference $\Delta V_N$ to a temperature $TEMP_N$.

Figure 12B:
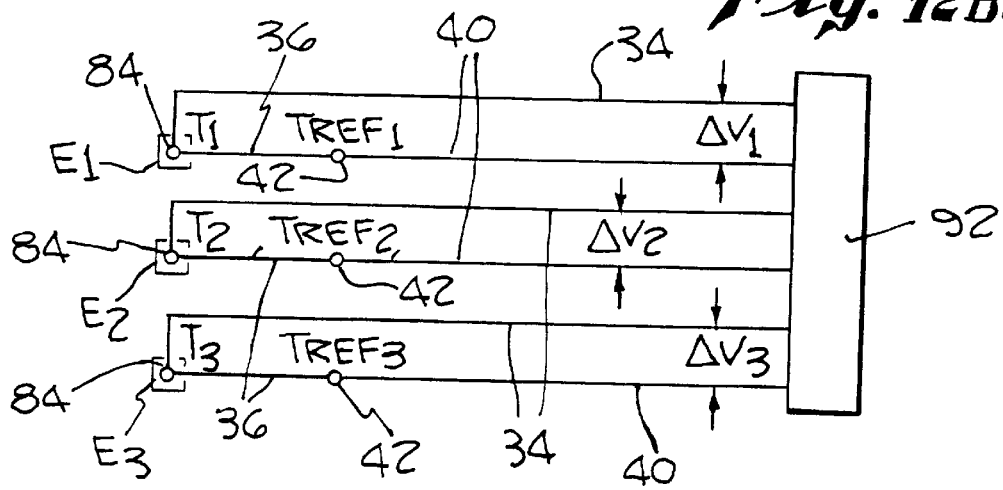

FIG. 12B schematically shows an alternative arrangement for electrically coupling three thermocouples $T_{1,2,3}$ for use in an ablating element. In FIG. 12B, individual lengths of copper wire 40 are electrically coupled in series with the constantan wires 36 of each thermocouple $T_{1,2,3}$, in the same manner described before. The individual junction regions 42 form three individual reference thermocouples $T_{REF\ 1,2,3}$, one for each thermocouple $T_{1,2,3}$. These junction regions 42 are each individually encapsulated within an epoxy or PTFE material, as already described. The three individual reference thermocouples $T_{REF\ 1,2,3}$ are commonly exposed to the same, known temperature condition.

As FIG. 12B shows, the temperature-related voltage differences $\Delta V_{1,2,3}$ are measured between the copper wire 34 of a selected thermocouple $T_{1,2,3}$ and the copper wire 40 of its associated reference thermocouple $T_{REF\ 1,2,3}$.

Figure 12C:
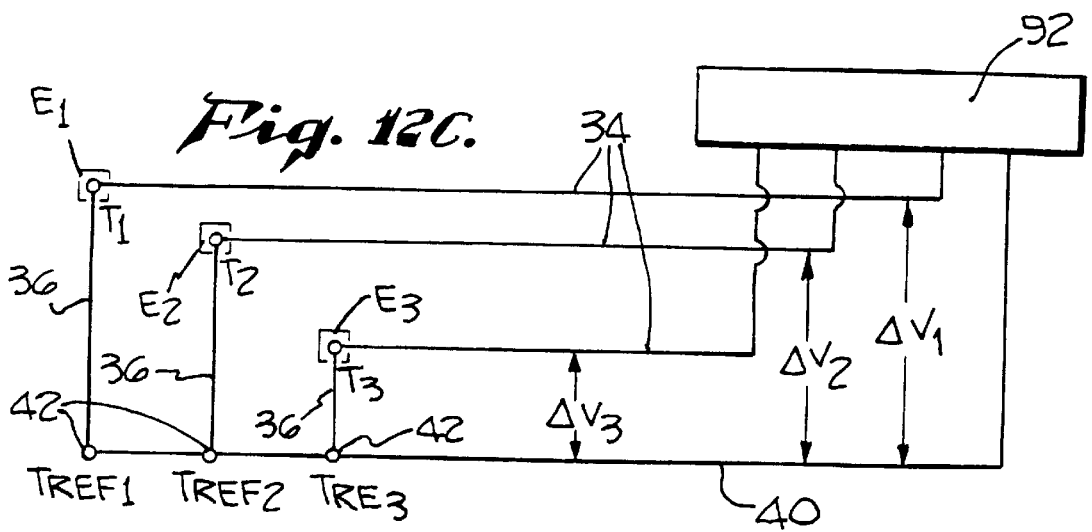

FIG. 12C schematically shows another alternative arrangement for electrically coupling three thermocouples $T_{1,2,3}$ for use in an ablating element. In FIG. 12C, a single length of copper wire 40 is electrically coupled in parallel with the constantan wires 36 of each thermocouple $T_{1,2,3}$. The individual electrical junction regions 42 form three individual reference thermocouples $T_{REF\ 1,2,3}$, one for each thermocouple $T_{1,2,3}$. As before described, the junction regions 42 are all individually encapsulated within an epoxy or PTFE material. As in the embodiment shown in FIG. 12B, the three individual reference thermocouples $T_{REF\ 1,2,3}$ are commonly exposed to the same, known temperature condition.

As FIG. 12C shows, the temperature-related voltage differences $\Delta V_{1,2,3}$ are measured between the copper wire 34 of a selected thermocouple $T_{1,2,3}$ and the copper wire 40 of its associated reference thermocouple $T_{REF\ 1,2,3}$.

Conventional practice would locate the common reference thermocouple $T_{REF}$ in the FIG. 12A embodiment and the three individual reference thermocouples $T_{REF\ 1,\ 2,\ 3}$ in the FIGS. 12B and 12C embodiments externally within the temperature processing element 92 itself. In these arrangements (which can be employed, if desired), the known temperature condition $TEMP_{REF}$ is the temperature to which the junction regions of the reference thermocouples are exposed. This ambient temperature condition can be measured by a thermistor in the processing element 92. Alternatively, a conventional compensation circuit can be used.

The common reference thermocouple $T_{REF}$ in the FIG. 12A embodiment and the three individual reference thermocouples $T_{REF\ 1,\ 2,\ 3}$ in the FIGS. 12B and 12C can also be carried within the handle 16 of the catheter probe 14. In this arrangement, the known temperature condition $TEMP_{REF}$ is the temperature to which the junction regions 42 of the reference thermocouples are exposed in the handle 16. This temperature condition can be measured by a thermistor in the handle 16 (not shown), or using a conventional compensation circuit. However, in the illustrated and preferred embodiment, the common reference thermocouple $T_{REF}$ in the FIG. 12A embodiment and the three reference thermocouples $T_{REF\ 1,\ 2,\ 3}$ in the FIGS. 12B and 12C embodiments are carried onboard the catheter body 12 for exposure to the blood pool in the body. In this preferred arrangement, all reference thermocouples are exposed to blood temperature, either by being located in a heart chamber, or by being located elsewhere in the vascular system of the patient where the catheter body lies. $TEMP_{REF}$ or $TEMP_{REF(1,2,3)}$ thereby is at or near 37° C.

Figure 13:
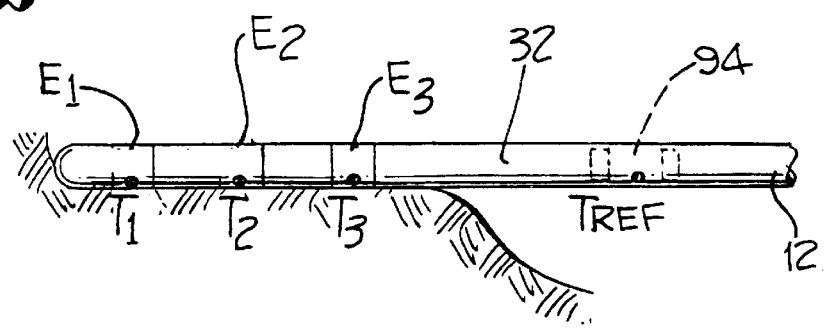
FIG. 13 is a side view of a flexible ablating element with multiple electrodes and multiple thermocouples, and further including an onboard reference thermocouple exposed to the blood pool.
Figure 14A:
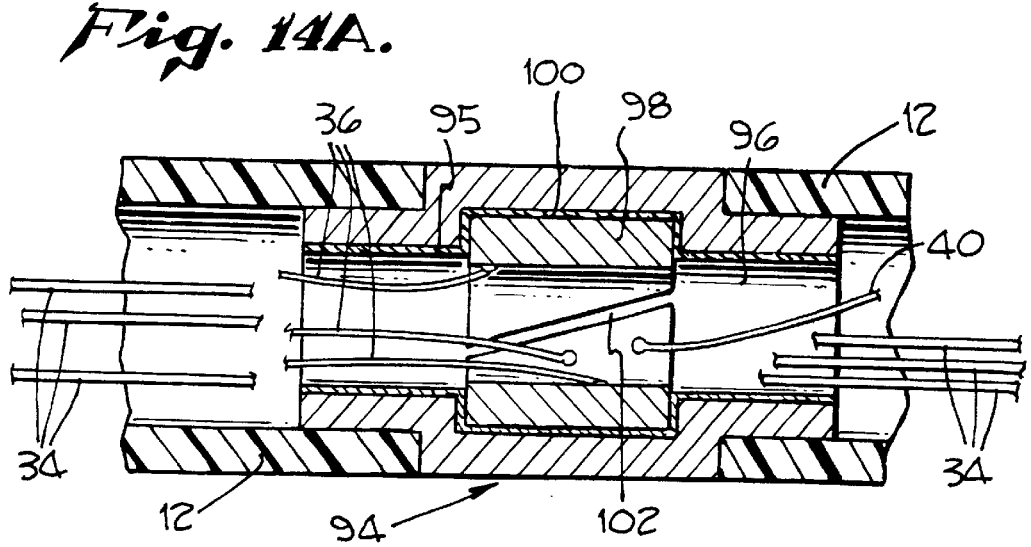
FIG. 14A is an enlarged side section view of an onboard reference thermocouple shown in FIG. 13.

FIGS. 13 and 14A show one preferred structural implementation of an onboard reference thermocouple in the arrangement shown schematically in FIG. 12A.

As FIG. 13 shows, a coupler member 94 carried by the catheter body 12 comprises the common reference thermocouple $T_{REF}$. The coupler member 94 is made of a biocompatible, thermally conductive material, like stainless steel or platinum.

As FIG. 13 shows, the coupler member 94 is secured in line onboard the catheter body 12 in a region spaced away from the ablating electrodes E1, E2, and E3. As before described, the coupler member 94 can either be located inside a heart chamber (as FIG. 13 shows), or elsewhere away from the ablating element 10 in the patient's vascular system where the catheter body 12 extends.

If located within the heart chamber itself (as FIG. 13 shows), the coupler member 94 should be spaced far enough away from the electrode elements E1/E2/E3 so that the blood pool contacting the coupler member 94 will not be subject to the localized blood heating effects of the ablation procedure. In this situation, as when the coupler member 94 is more distantly located outside the heart chamber, the temperature of the blood pool contacting the coupler member 94 will remain essentially constant at about 37° C. during the ablation procedure.

As FIG. 14A shows in detail, the coupler member 94 includes an interior bore 96, which is coated with an electrically insulating material 95. A ring 98 is seated in a groove 100 within the bore 96.

The coupler member 94 and ring 98 can comprise a one-piece assembly (as FIG. 14A shows). In this arrangement, the ring 98 includes a split 102 for reducing its diameter, so it can be pressed into and compression-fitted in place within the groove 100. Alternatively, the coupler member 94 can comprise a two part body, separable along the groove 100, to allow placement of the ring 98. These arrangements allow the electrical connections to the ring 98 to be made outside the member 94, before placement therein.

In the embodiment shown in FIG. 14A, the ring 98 is made of constantan metal. The ring 98 thereby structurally corresponds to the length of constantan wire 38 shown in FIG. 12A, to which the constantan wires 36 of the three thermocouples $T_{1,2,3}$ are electrically coupled in parallel, as FIG. 14A shows. The length of copper wire 40 (as shown in FIG. 12A) is electrically coupled to the ring 98 (as FIG. 14A also shows).

This copper wire 40 and the copper wires 34 from each thermocouple $T_{1,\ 2,\ 3}$ pass through the bore of the catheter body 12 to the external temperature processing element 92 (via the external connector 104 carried on the handle 16, as FIG. 1 shows. The coupler member 94 and ring 98 thereby serve as an in-line reference thermocouple $T_{REF}$ common to the thermocouples $T_{1,\ 2,\ 3}$.

Figure 14B:
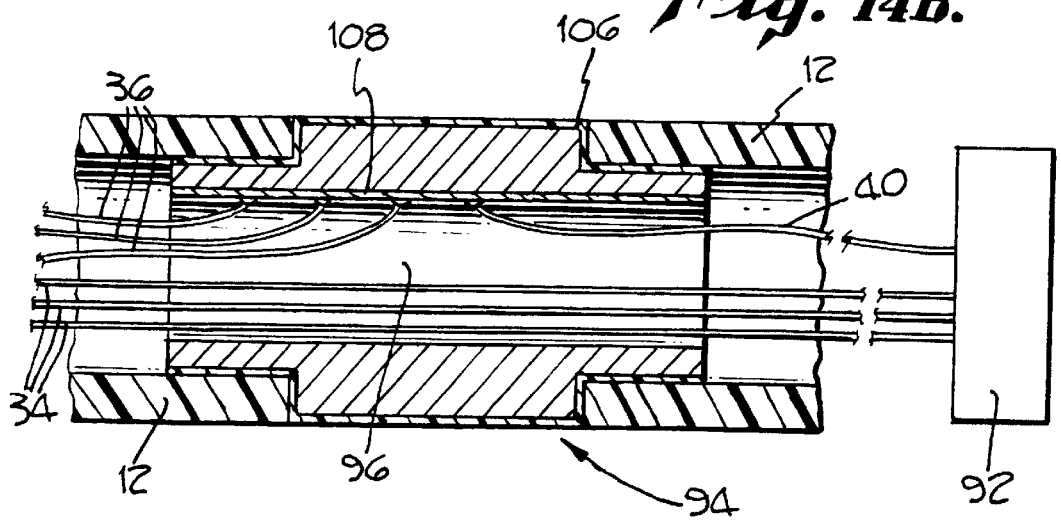
FIG. 14B is an enlarged side section view of an alternative embodiment of an onboard reference thermocouple shown in FIG. 13.

FIG. 14B shows an alternative embodiment for the coupler member 94 that is free of an interior ring 98. In FIG. 14B, the exterior surface of the coupler member 94 is coated with an epoxy or TFE material 106, as previously described. The material 106 bonds the catheter body 12 to the opposite ends of the coupler member 94. The material 106 also electrically insulates the coupler member 94 from the ablating electrodes 30.

The coupler member 94 in FIG. 14B also includes an interior bore 96. The bore 96 has an inner surface region where a layer 108 of constantan material is applied. This layer 108 corresponds to the length of constantan wire 40 shown in FIG. 12A, to which the constantan wires 36 of the three thermocouples $T_{1,2,3}$ are electrically coupled in parallel. The copper wire 40 for the reference thermocouple $T_{REF}$ is also fused to the constantan layer 108.

The constantan ring 98 in FIG. 14A and the constantan layer 108 in FIG. 14B collectively couple the constantan wires 34 of each electrode thermocouple $T_{1,2,3}$ to the copper wire 40 of the reference thermocouple $T_{REF}$. It thereby simplifies electrical connections within the confined interior regions of the small diameter of the catheter body 12. The constantan ring 98 and layer 108 also eliminate the need to pass the constantan wires 36 of each electrode thermocouple $T_{1,\ 2,\ 3}$ through the entire length of the catheter body 12.

The temperature condition that the onboard reference thermocouple $T_{REF}$ senses is the essentially constant temperature of the blood pool, which the coupler member 94, exposed to the blood pool, thermally conducts. The reference temperature $TEMP_{REF}$ is thereby not subject to sudden change or variance, as external ambient air temperature can be. Greater accuracy results.

FIGS. 15A and 15B show an alternative embodiment for using a single reference thermocouple. The constantan wire 36 from the thermocouples $T_{1,\ 2,\ 3}$ are connected together by either a weld or solder connection to the constantan wire 38 in a star configuration (shown in FIGS. 15A/B), although other configurations (such as a ladder configuration) can be used. The reference thermocouple $T_{REF}$ can then be placed under a ring, just like the thermocouples used for temperature sensing. All the thermocouple wires are then wrapped in a tube 114 to thermally and electrically insulate them from the RF wires (not shown). FIG. 15B is the schematic representation of the star connection of FIG. 15A.

FIGS. 16A and 16B show a preferred structural implementation of multiple onboard reference thermocouples $T_{REF,1,2,3}$ electrically coupled in the arrangement shown schematically in FIG. 12B. As FIG. 16A shows, the three reference thermocouples $T_{REF\ 1,2,3}$ are individually threaded through the catheter body 12 and encapsulated in a electrically insulating and thermally conducting epoxy bubble 110. Preferably, the thermocouples $T_{REF\ 1,2,3}$ are spaced closely together.

As FIG. 16B shows, the number of wires entering the processing element 92 is reduced from six to four by electrically coupling the three copper wires 40 associated with the reference thermocouples $T_{REF\ 1,2,3}$ within the handle 16 of the probe. This forms a single copper wire 112 common to all the reference thermocouples. The common reference copper wire 112 and the three other copper wires 34 of the thermocouples $T_{1,2,3}$, are connected to the processing element 92 (as FIG. 16B shows). In this arrangement (as FIG. 16B further shows), $\Delta V_{1,2,3}$ is measured between the individual copper wires 34 for each thermocouple $T_{1,2,3}$ and the common reference copper wire 112 of the reference thermocouples $T_{REF1,2,3}$.

The arrangement of multiple onboard reference thermocouples $T_{REF\ 1,2,3}$ in the arrangement shown schematically in FIG. 12C can be structurally carried out using a coupler member 94 and ring 98 assembly identical to the one shown in FIG. 14, except that the ring 98 is made of copper metal to correspond to the common copper wire 40 shown FIG. 12C. Alternatively, the multiple onboard reference thermocouples $T_{REF\ 1,2,3}$ in the arrangement shown schematically in FIG. 12C can be structurally implemented using the ring-free coupler member 94 shown in FIG. 15, except that the layer 108 within the coupler bore 96 is made of copper metal to correspond to the common copper wire 40 shown in FIG. 12C.

All of the thermocouple assemblies described in FIGS. 12A, B, and C require an initialization before conducting an ablation procedure. The temperature processing element 92 goes through this initialization phase to compensate for offsets in the voltage differences $\Delta V_{1,2,3}$ at blood temperature.

During the ablating procedure, the temperature processing element 92 registers the individual change in voltage $\Delta V_{1,2,3}$. The temperature processing element 92 applies the associated offset and then converts the resulting change in voltages $\Delta V_{1,2,3}$ to temperature readings, using a preestablished look-up table, as already described.

The temperature processing element 92 preferably displays as output the temperature conditions sensed along the ablating element 10. The multiple sensed temperature conditions can also be used in a feedback control loop to control the ablation process itself. This aspect of the invention will be described in greater detail later.

In the preferred embodiment, regardless of the particular type of thermocouple used and the manner in which it is electrically wired within the catheter body 12, the wires 34/36 and 38/40 serving the thermocouples are wrapped in a tube 114 (see FIG. 16A) of thermally insulating material, like polyimide. The tube 114 thermally insulates the thermocouple wires from other wires in the body that carry ablating energy. Thus, the thermocouple wires are thermally insulated from heat that may be generated within the catheter body 12 by the transfer of ablating energy to the energy emitting regions at the distal end of the catheter body. The temperature-indicating voltages generated by the thermocouples are thereby not altered by exposure of the thermocouple wires to this source of heat within the catheter body.

B. Low Profile Composite Thermocouple

Figure 17:
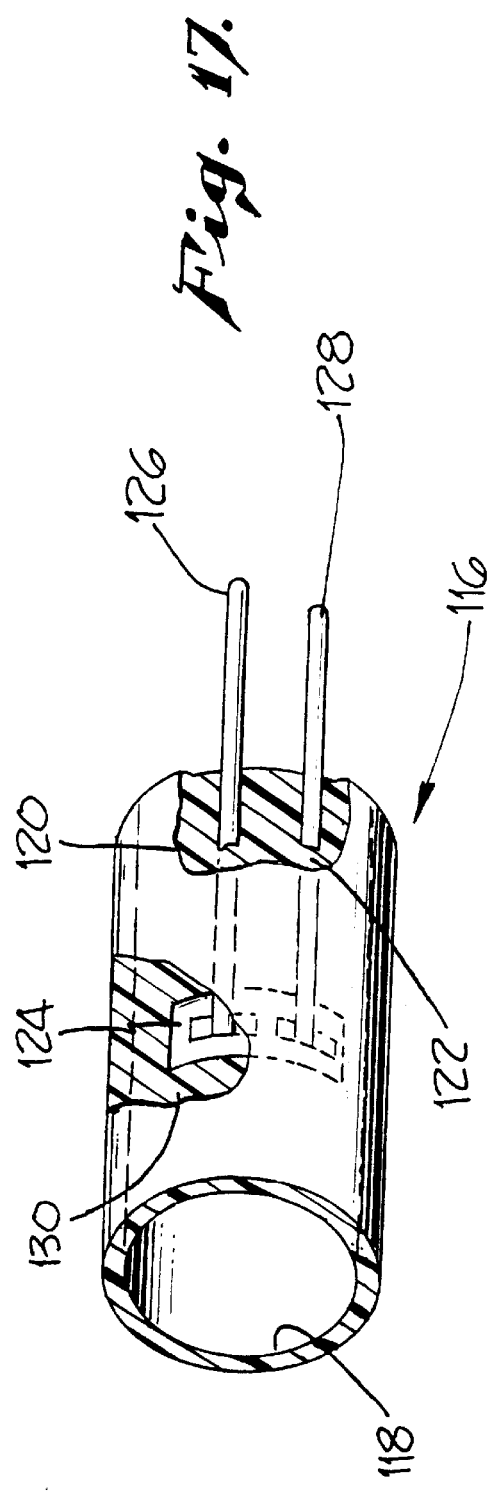
FIG. 17 is a perspective end view, with portions broken away and in section, of a composite flexible thermocouple usable in association with a flexible ablating element.

FIG. 17 shows a composite, low profile thermocouple 116 that can be used in association with all types of flexible ablating elements 10. The thermocouple 116 comprises a thin, semi-flexible substrate 118 formed of an electrically insulating material, like polyimide. In the illustrated embodiment, the substrate 118 is tubular in shape. Of course, other shapes could be used.

Two electrical conductive pathways 120 and 122 extend along the surface of the substrate 118. The pathways 120 and 122 can be applied by conventional sputter coating techniques or an ion beam assisted deposition (IBAD) process. Alternatively, small gauge wires of these different metal materials could be embedded within the tubular substrate during its extrusion or molding.

Each pathway 120 and 122 comprises a different electrically conductive metal material. Preferably, one pathway 120 is formed by applying copper, and the other pathway 122 is formed by applying constantan.

The ends of the two pathways 120 and 122 are electrically fused together on the substrate 118. In the illustrated and preferred embodiment, a band 124 of metal material of one of the pathways 120 and 122 spans the ends of the pathways 120 and 122, electrically fusing them together. This band 124 forms a thermocouple junction on the surface of the substrate 118. Small gauge wires 126 and 128 of matching metal material are electrically coupled to the opposite ends of the pathways 120 and 122.

A thin, outer electrically insulating layer 130 is applied over the pathways 120 and 122 and thermocouple band 124 to complete the assembly of the low profile thermocouple 116.

Additional pathways 120/122, bands 124, and wires 126/128 can be applied to a single substrate 118 to form multiple thermocouple junctions on it.

Figure 18:
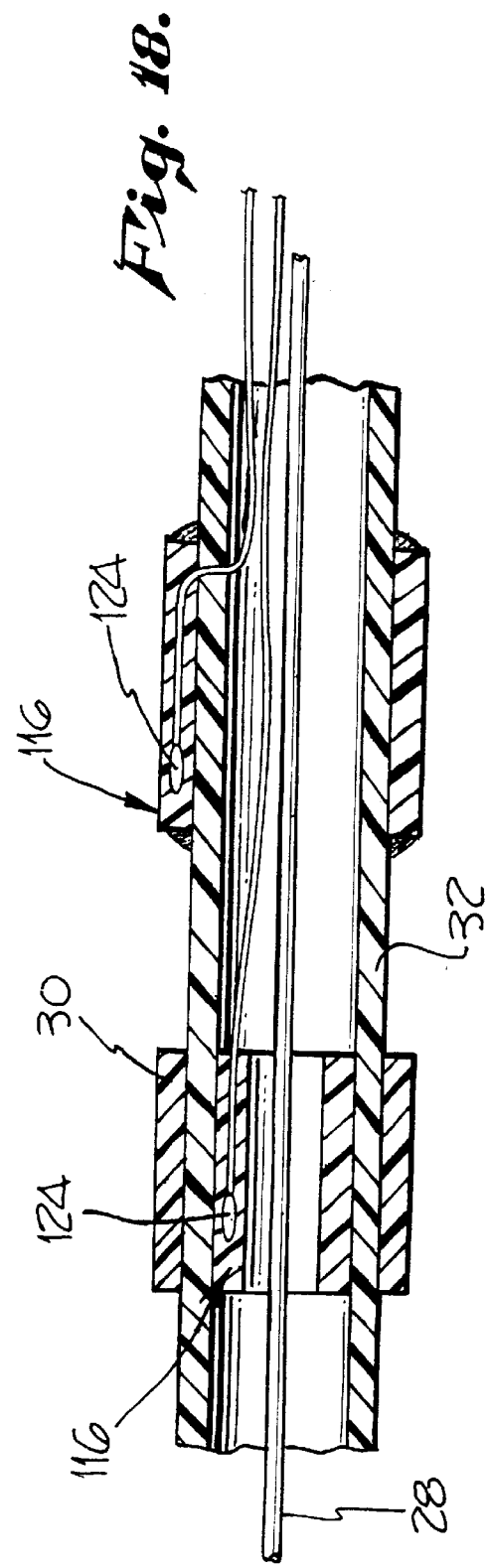
FIG. 18 is a side section view of the flexible thermocouple in use in association with a flexible ablating element.

As FIG. 18 shows, the semi-flexible thermocouple 116 can be made small enough in diameter to fit within the structure 10 beneath or near an ablating element 30. Alternatively, the thermocouple 116 can be made large enough in diameter to fit over the flexible body 32, as FIG. 18 also shows.

III. Control of Cardiac Ablation Using Multiple Temperature Feedback Control FIG. 19 shows, in schematic form, a system 200 for applying ablating energy by multiple emitters based, at least in part, upon local temperature conditions sensed by multiple sensing elements 80.

Figure 19:
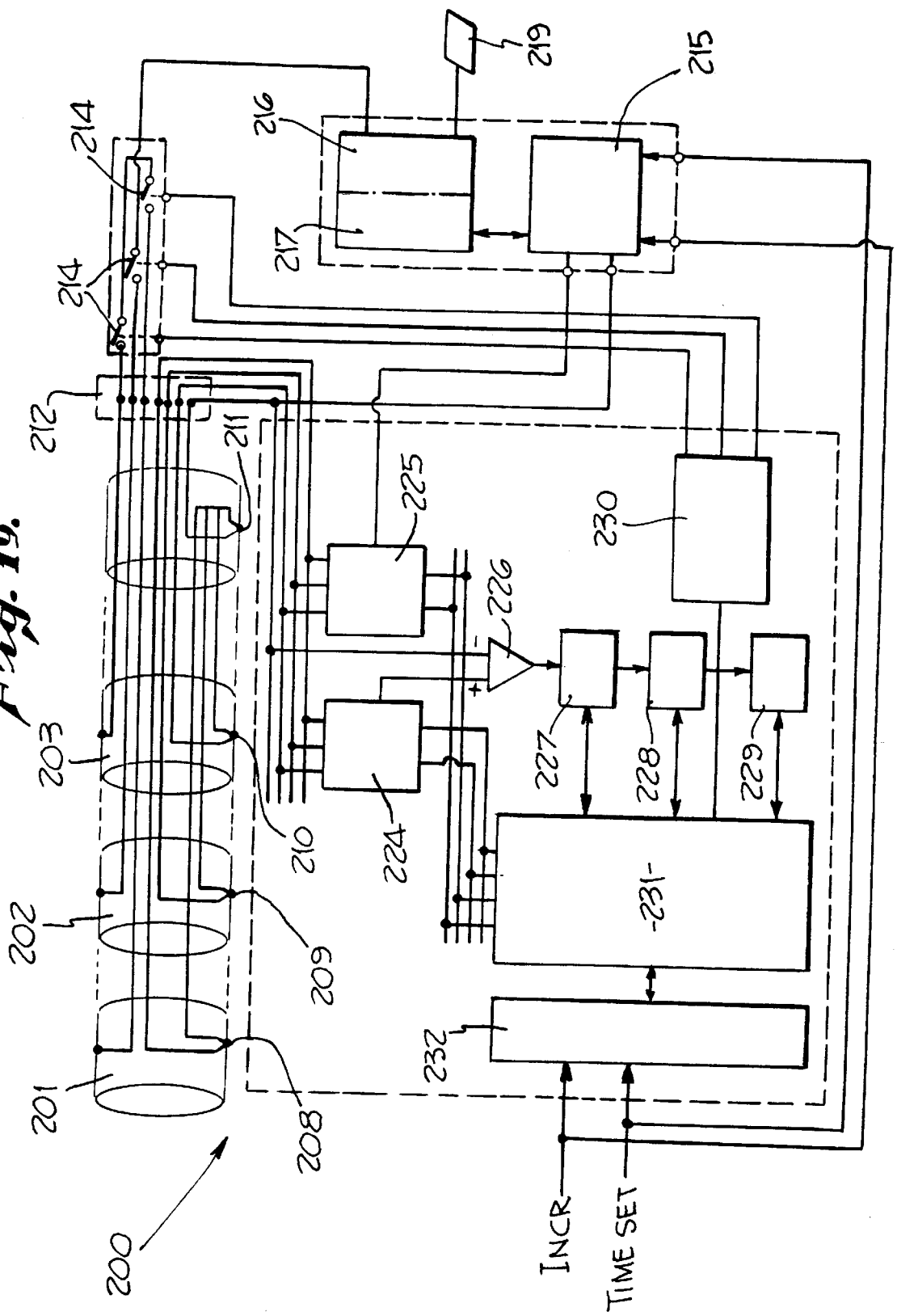
FIGS. 19 and 20 are schematic views of a system for controlling the application of ablating energy to multiple electrodes using multiple temperature sensing inputs.

In FIG. 19, the multiple sensing elements 80 comprise thermocouples 208, 209, and 210 individually associated with the multiple emitters of ablating energy, which comprise electrode regions 201, 202, and 203. The system 200 also includes a common reference thermocouple 211 carried within the coupler element 211 for exposure to the blood pool, as previously described. Alternatively, other kinds of temperature sensing elements can be used, like, for example, thermistors, fluoroptic sensors, and resistive temperature sensors, in which case the reference sensor 211 would typically not be required.

The system 200 further includes an indifferent electrode 219 for operation in a unipolar mode.

The ablating energy emitters 201, 202, 203 can comprise the rigid electrode segments 30 previously described. Alternatively, the electrode regions 201, 202, 203 can comprise a continuous or segmented flexible electrode of wrapped wire or ribbon. It should be appreciated that the system 200 can be used in association with any ablating element that employs multiple, independently actuated ablating elements.

The system 200 includes a source 217 of ablating energy. In FIG. 19, the source 217 generates radio frequency (RF) energy. The source 217 is connected (through a conventional isolated output stage 216) to an array of power switches 214, one for each electrode region 201, 202, and 203. A connector 212 (carried by the probe handle) electrically couples each electrode region 201, 203, 203 to its own power switch 214 and to other parts of the system 200.

The system 200 also includes a microcontroller 231 coupled via an interface 230 to each power switch 214. The microcontroller 231 turns a given power switch 214 on or off to deliver RF power from the source 217 individually to the electrode regions 201, 202, and 203. The delivered RF energy flows from the respective electrode region 201, 202, and 203, through tissue, to the indifferent electrode 219, which is connected to the return path of the isolated output stage 216.

Figure 20:
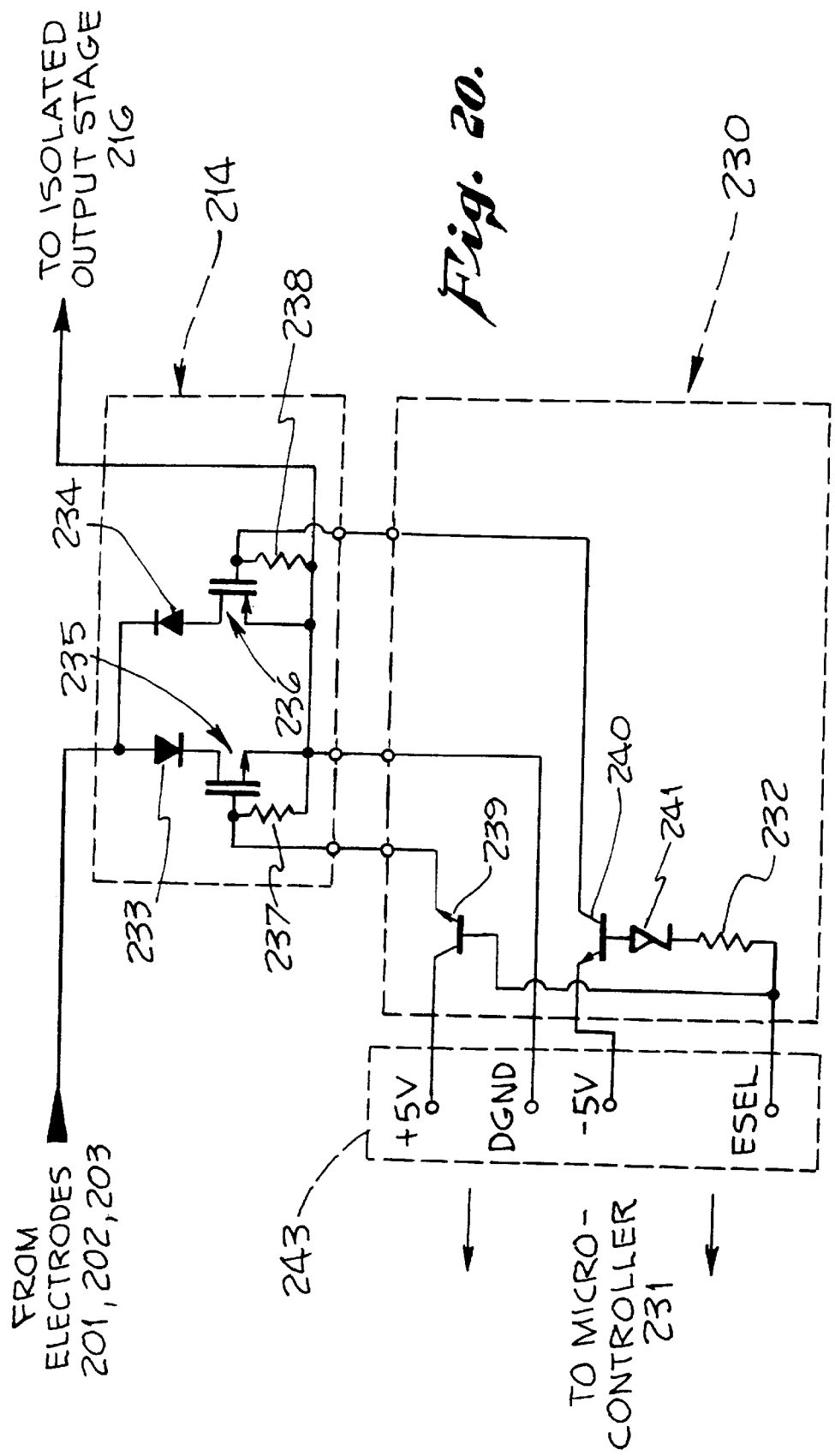

The power switch 214 and interface 230 configuration can vary according to the type of ablating energy being applied. FIG. 20 shows a representative implementation for applying RF ablating energy.

In this implementation, each power switch 214 includes an N-MOS power transistor 235 and a P-MOS power transistor 236 coupled in between the respective electrode region 201, 202, and 203 and the isolated output stage 216 of the power source 217.

A diode 233 conveys the positive phase of RF ablating energy to the electrode region. A diode 234 conveys the negative phase of the RF ablating energy to the electrode region. Resistors 237 and 238 bias the N-MOS and P-MOS power transistors 235 and 236 in conventional fashion.

The interface 230 for each power switch 214 includes two NPN transistors 239 and 240. The emitter of the NPN transistor 239 is coupled to the gate of the N-MOS power transistor 235. The collector of the NPN transistor 240 is coupled to the gate of the P-MOS power transistor 280.

The interface for each power switch 214 also includes a control bus 243 coupled to the microcontroller 231. The control bus 243 connects each power switch 214 to digital ground (DGND) of the microcontroller 231. The control bus 243 also includes a (+) power line (+5 V) connected to the collector of the NPN transistor 239 and a (−) power line (−5 V) connected to the emitter of the NPN interface transistor 240.

The control bus 243 for each power switch 214 further includes an $E_{SEL}$ line. The base of the NPN transistor 239 is coupled to the $E_{SEL}$ line of the control bus 243. The base of the NPN transistor 240 is also coupled the $E_{SEL}$ line of the control bus 243 via the Zener diode 241 and a resistor 232. $E_{SEL}$ line connects to the cathode of the Zener diode 241 through the resistor 232. The Zener diode 241 is selected so that the NPN transistor 240 turns on when $E_{SEL}$ exceeds about 3 volts (which, for the particular embodiment shown, is logic 1).

It should be appreciated that the interface 230 can be designed to handle other logic level standards. In the particular embodiment, it is designed to handle conventional TTL (transistor transfer logic) levels.

The microcontroller 231 sets $E_{SEL}$ of the control bus 243 either at logic 1 or at logic 0. At logic 1, the gate of the N-MOS transistor 235 is connected to (+) 5 volt line through the NPN transistors 239. Similarly, the gate of the P-MOS transistor 236 is connected to the (−) 5 volt line through the NPN transistor 240. This conditions the power transistors 235 and 236 to conduct RF voltage from the source 217 to the associated electrode region. The power switch 214 is "on."

When the microcontroller 231 sets $E_{SEL}$ at logic 0, no current flows through the NPN transistors 239 and 240. This conditions the power transistors 235 and 236 to block the conduction of RF voltage to the associated electrode region. The power switch 214 is "off."

The system 200 (see FIG. 19) further includes two analog multiplexers (MUX) 224 and 225. The multiplexers 224 and 225 receive voltage input from each thermocouple 208, 209, 210, and 211. The microcontroller 231 controls both multiplexers 224 and 225 to select voltage inputs from the multiple temperature sensing thermocouples 208, 209, 210, and 211.

The voltage inputs from the thermocouples 208, 209, 210, and 211 are sent to front end signal conditioning electronics. The inputs are amplified by differential amplifier 226, which reads the voltage differences between the copper wires of the thermocouples 208/209/210 and the reference thermocouple 211. The voltage differences are conditioned by element 227 and converted to digital codes by the analog-to-digital converter 228. The look-up table 229 converts the digital codes to temperature codes. The temperature codes are read by the microcontroller 231.

The microcontroller 231 compares the temperature codes for each thermocouple 208, 209, and 210 to preselected criteria to generate feedback signals. The preselected criteria are inputted through a user interface 232. These feedback signals control the interface power switches 214 via the interface 230, turning the electrodes 201, 202, and 203 off and on.

The other multiplexer 225 connects the thermocouples 208, 209, 210, and 211 selected by the microcontroller 231 to a temperature controller 215. The temperature controller 215 also includes front end signal conditioning electronics, as already described with reference to elements 226, 227, 228, and 229. These electronics convert the voltage differences between the copper wires of the thermocouples 208/209/210 and the reference thermocouple 211 to temperature codes. The temperature codes are read by the controller and compared to preselected criteria to generate feedback signals. These feedback signals control the amplitude of the voltage (or current) generated by the source 217 for delivery to the electrodes 201, 202, and 203.

Based upon the feedback signals of the microcontroller 231 and the temperature controller 215, the system 200 distributes power to the multiple electrode regions 201, 202, and 203 to establish and maintain a uniform distribution of temperatures along the ablating element. In this way, the system 200 obtains safe and efficacious lesion formation using multiple emitters of ablating energy.

The system 200 can control the delivery of ablating energy in different ways. Several representative modes will now be described.

Individual Amplitudes/Collective Duty Cycle

The electrode regions 201, 202, and 203 will be symbolically designated E(J), where J represents a given electrode region (J=1 to N).

As before described, each electrode region E(J) has at least one temperature sensing element 208, 209, and 210, which will be designated S(J,K), where J represents the electrode region and K represents the number of temperature sensing elements on each electrode region (K=1 to M).

Figure 21:
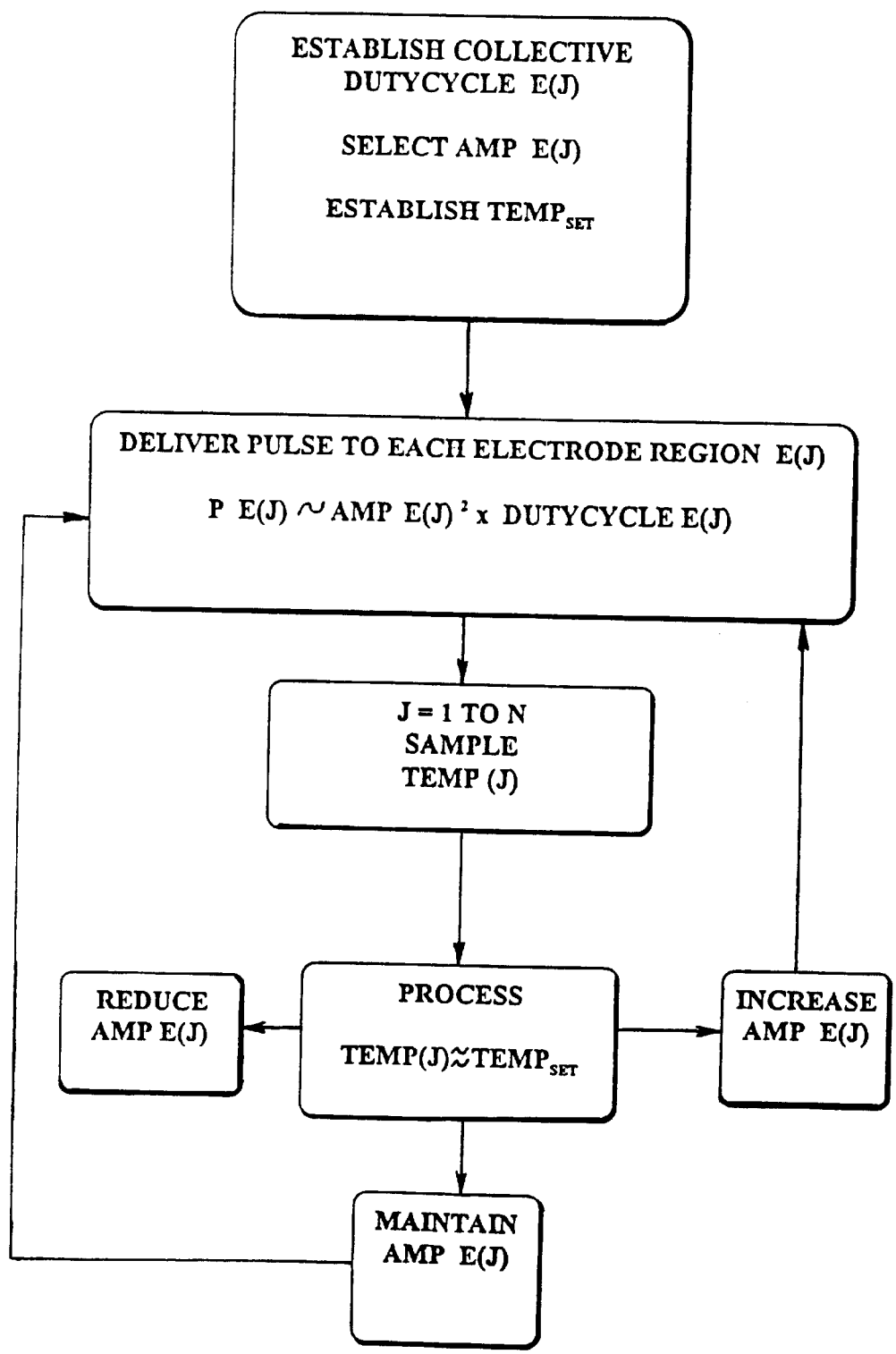
FIG. 21 is a schematic flow chart showing an implementation of the temperature feedback controller shown in FIGS. 19 and 20, using individual amplitude control with collective duty cycle control.

In this mode (see FIG. 21), the microcontroller 231 operates the power switch interface 230 to deliver RF power from the source 217 in multiple pulses of duty cycle 1/N.

With pulsed power delivery, the amount of power ($P_{E(J)}$) conveyed to each individual electrode region E(J) is expressed as follows:

$$P_{E(J)} \sim AMP_{E(J)}^2 \times DUTYCYCLE_{E(J)}$$

where:

$AMP_{E(J)}$ is the amplitude of the RF voltage conveyed to the electrode region E(J), and $DUTYCYCLE_{E(J)}$ is the duty cycle of the pulse, expressed as follows:

$$DUTYCYCLE_{E(J)} = \frac{TON_{E(J)}}{TON_{E(J)} + TOFF_{E(J)}}$$

where:

$TON_{E(J)}$ is the time that the electrode region E(J) emits energy during each pulse period, $TOFF_{E(J)}$ is the time that the electrode region E(J) does not emit energy during each pulse period.

The expression $TON_{E(J)} + TOFF_{E(J)}$ represents the period of the pulse for each electrode region E(J).

In this mode, the microcontroller 231 collectively establishes duty cycle (DUTYCYCLE$_{E(J)}$) of 1/N for each electrode region (N being equal to the number of electrode regions).

The microcontroller 231 may sequence successive power pulses to adjacent electrode regions so that the end of the duty cycle for the preceding pulse overlaps slightly with the beginning of the duty cycle for the next pulse. This overlap in pulse duty cycles assures that the source 217 applies power continuously, with no periods of interruption caused by open circuits during pulse switching between successive electrode regions.

In this mode, the temperature controller 215 makes individual adjustments to the amplitude of the RF voltage for each electrode region (AMP$_{E(J)}$), thereby individually changing the power P$_{E(J)}$ of ablating energy conveyed during the duty cycle to each electrode region, as controlled by the microcontroller 231.

In this mode, the microcontroller 231 cycles in successive data acquisition sample periods. During each sample period, the microcontroller 231 selects individual sensors S(J,K), and voltage differences are read by the controller 215 (through MUX 225) and converted to temperature codes TEMP(J).

When there is more than one sensing element associated with a given electrode region, the controller 215 registers all sensed temperatures for the given electrode region and selects among these the highest sensed temperature, which constitutes TEMP(J). The temperature sensing element providing the highest sensed temperature for a given electrode region is the one in most intimate contact with heart tissue. The lower sensed temperatures of the other sensing elements on the given electrode region indicate that the other sensing elements are not in such intimate contact, and are instead exposed to convective cooling in the blood pool.

In this mode, the controller 215 compares the temperature TEMP(J) locally sensed at each electrode E(J) during each data acquisition period to a setpoint temperature TEMP$_{SET}$ established by the physician. Based upon this comparison, the controller 215 varies the amplitude AMP$_{E(J)}$ of the RF voltage delivered to the electrode region E(J), while the microcontroller 231 maintains the DUTYCYCLE$_{E(J)}$ for that electrode region and all other electrode regions, to establish and maintain TEMP(J) at the setpoint temperature TEMP$_{SET}$.

The set point temperature TEMP$_{SET}$ can vary according to the judgment of the physician and empirical data. A representative set point temperature for cardiac ablation is believed to lie in the range of 40° C. to 95° C., with 70° C. being a representative preferred value.

The manner in which the controller 215 governs AMP$_{E(J)}$ can incorporate proportional control methods, proportional integral derivative (PID) control methods, or fuzzy logic control methods.

For example, using proportional control methods, if the temperature sensed by the first sensing element TEMP(1) >TEMP$_{SET}$, the control signal generated by the controller 215 individually reduces the amplitude AMP$_{E(1)}$ of the RF voltage applied to the first electrode region E(1), while the microcontroller 231 keeps the collective duty cycle DUTYCYCLE$_{E(1)}$ for the first electrode region E(1) the same. If the temperature sensed by the second sensing element TEMP(2)<TEMP$_{SET}$, the control signal of the controller 215 increases the amplitude AMP$_{E(2)}$ of the pulse applied to the second electrode region E(2), while the microcontroller 231 keeps the collective duty cycle DUTYCYCLE$_{E(2)}$ for the second electrode region E(2) the same as DUTYCYCLE$_{E(1)}$, and so on. If the temperature sensed by a given sensing element is at the set point temperature TEMP$_{SET}$, no change in RF voltage amplitude is made for the associated electrode region.

The controller 215 continuously processes voltage difference inputs during successive data acquisition periods to individually adjust AMP$_{E(J)}$ at each electrode region E(J), while the microcontroller 231 keeps the collective duty cycle the same for all electrode regions E(J). In this way, the mode maintains a desired uniformity of temperature along the length of the ablating element.

Using a proportional integral differential (PID) control technique, the controller 215 takes into account not only instantaneous changes that occur in a given sample period, but also changes that have occurred in previous sample periods and the rate at which these changes are varying over time. Thus, using a PID control technique, the controller 215 will respond differently to a given proportionally large instantaneous difference between TEMP (J) and TEMP$_{SET}$, depending upon whether the difference is getting larger or smaller, compared to previous instantaneous differences, and whether the rate at which the difference is changing since previous sample periods is increasing or decreasing.

Collective Amplitude/Individual Duty Cycles

Figure 22:
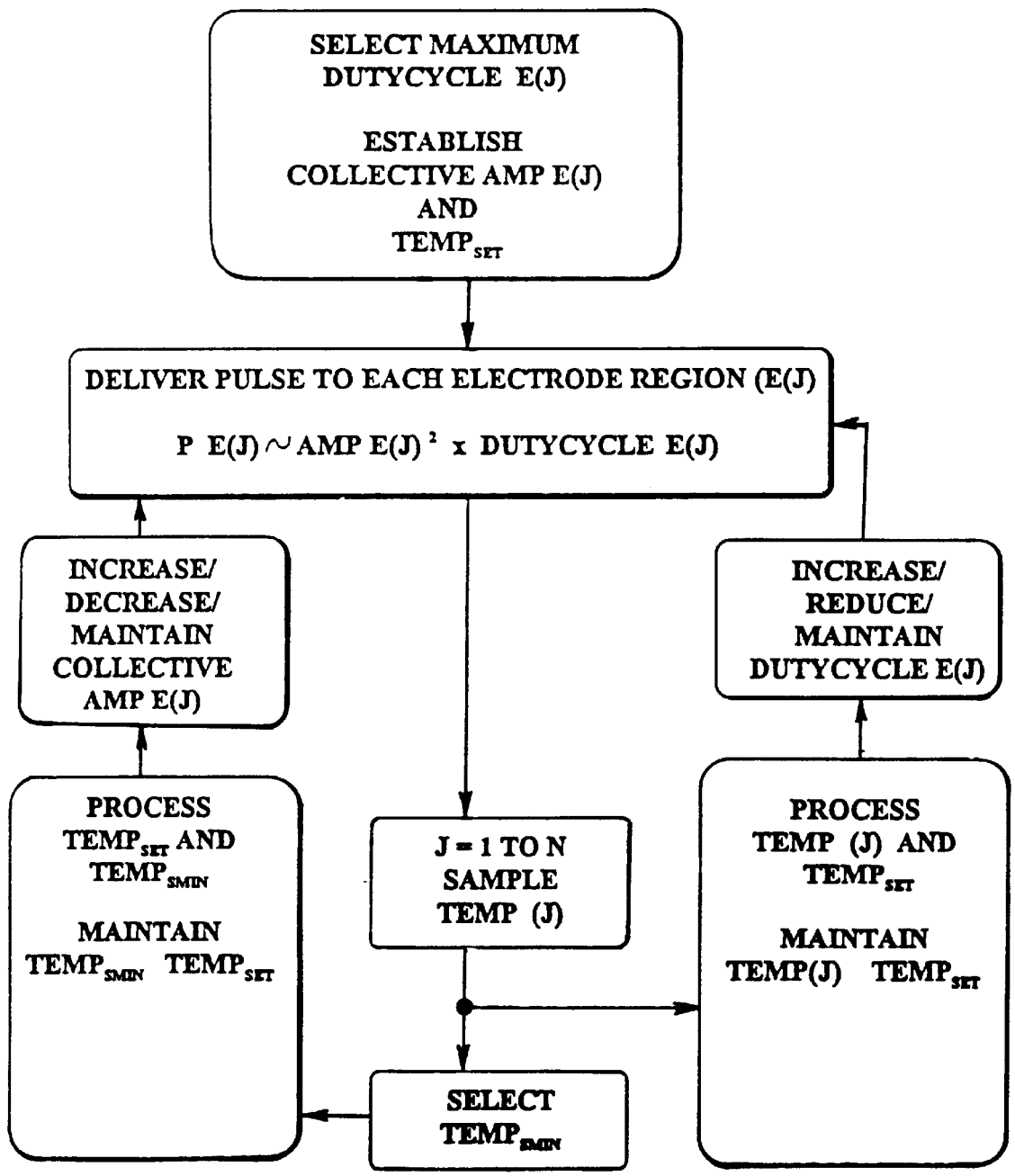
FIG. 22 is a schematic flow chart showing an implementation of the temperature feedback controller shown in FIGS. 19 and 20, using individual duty cycle control with collective amplitude control.

In this feedback mode (see FIG. 22), the controller 215 governs the source 217 to collectively control the RF voltage amplitude AMP$_{E(J)}$ for all electrode regions based upon the lowest local temperature sensed TEMP$_{SMIN}$. At the same time, in this feedback mode, the microcontroller 231 individually alters the power conveyed to the electrode regions where temperatures greater than TEMP$_{SMIN}$ are sensed, by adjusting the duty cycle DUTYCYCLE$_{E(J)}$ of these electrode regions.

In this mode, as in the previous mode, the microcontroller 231 separates the power into multiple pulses. Initially, each pulse has the same duty cycle (DUTYCYCLE$_{E(J)}$) of 1/N. As in the previous mode, the application of successive RF pulses to adjacent electrode regions may be timed to overlap so that the source 318 applies power continuously to the electrode regions E(J).

The controller 215 cycles in successive data acquisition periods to sequentially read the temperature sensed by each sensing element TEMP(J). When there are multiple sensing elements associated with each electrode region, the controller 215 registers all sensed temperatures for the particular electrode and selects among these the highest sensed temperature, which is TEMP(J).

In this mode, the controller 215 compares, during each data acquisition period, the individual temperatures sensed TEMP(J) to the set point temperature TEMP$_{SET}$. The controller 215 also selects the lowest sensed temperature TEMP$_{SMIN}$. The controller 215 adjusts AMP$_{E(J)}$ to maintain TEMP$_{SMIN}$≈TEMP$_{SET}$, using proportional, PID, or fuzzy logic control techniques. At the same time, the microcontroller 231 adjusts DUTYCYCLE$_{E(J)}$ of the electrode regions where TEMP(J)>TEMP$_{SMIN}$ to maintain TEMP(J) ≈TEMP$_{SET}$.

For example, using only proportional control techniques, if TEMP$_{SMIN}$<TEMP$_{SET}$, the controller 215 collectively increases the amplitude of the RF voltage of all electrode regions, based upon the difference between TEMP$_{SMIN}$ and TEMP$_{SET}$ (ΔTEMP$_{SMIN/SET}$), until TEMP$_{SMIN}$>TEMP$_{SET}$.

During this time (when TEMP$_{SMIN}$ remains below TEMP$_{SET}$), the microcontroller 231 also controls the application of power to the other electrode regions E(J) where the local sensed temperature TEMP(J) is above TEMP$_{SMIN}$, as follows:

(i) if TEMP(J)<TEMP$_{SET}$, the microcontroller 231 increases the duty cycle of the power applied to the electrode region E(J) at the RF voltage amplitude established by ΔTEMP$_{SMIN/SET}$.

(ii) if TEMP(J)>TEMP$_{SET}$, the microcontroller 231 decreases the duty cycle of the power applied to the electrode region E(J) at the RF voltage amplitude established by ΔTEMP$_{SMIN/SET}$.

(iii) if TEMP$_{S(N)}$=TEMP$_{SET}$, the microcontroller 231 maintains the duty cycle for the given electrode region E(N) at the RF voltage amplitude established by ΔTEMP$_{SMIN/SET}$.

When TEMP$_{SMIN}$>TEMP$_{SET}$, the controller 215 collectively reduces the RF voltage amplitude delivered to all electrode regions. When TEMP$_{SMIN}$=TEMP$_{SET}$, the controller 215 collectively maintains the then-established RF voltage amplitude delivered to all electrode regions.

Temperature Control with Hysteresis

Figure 23:
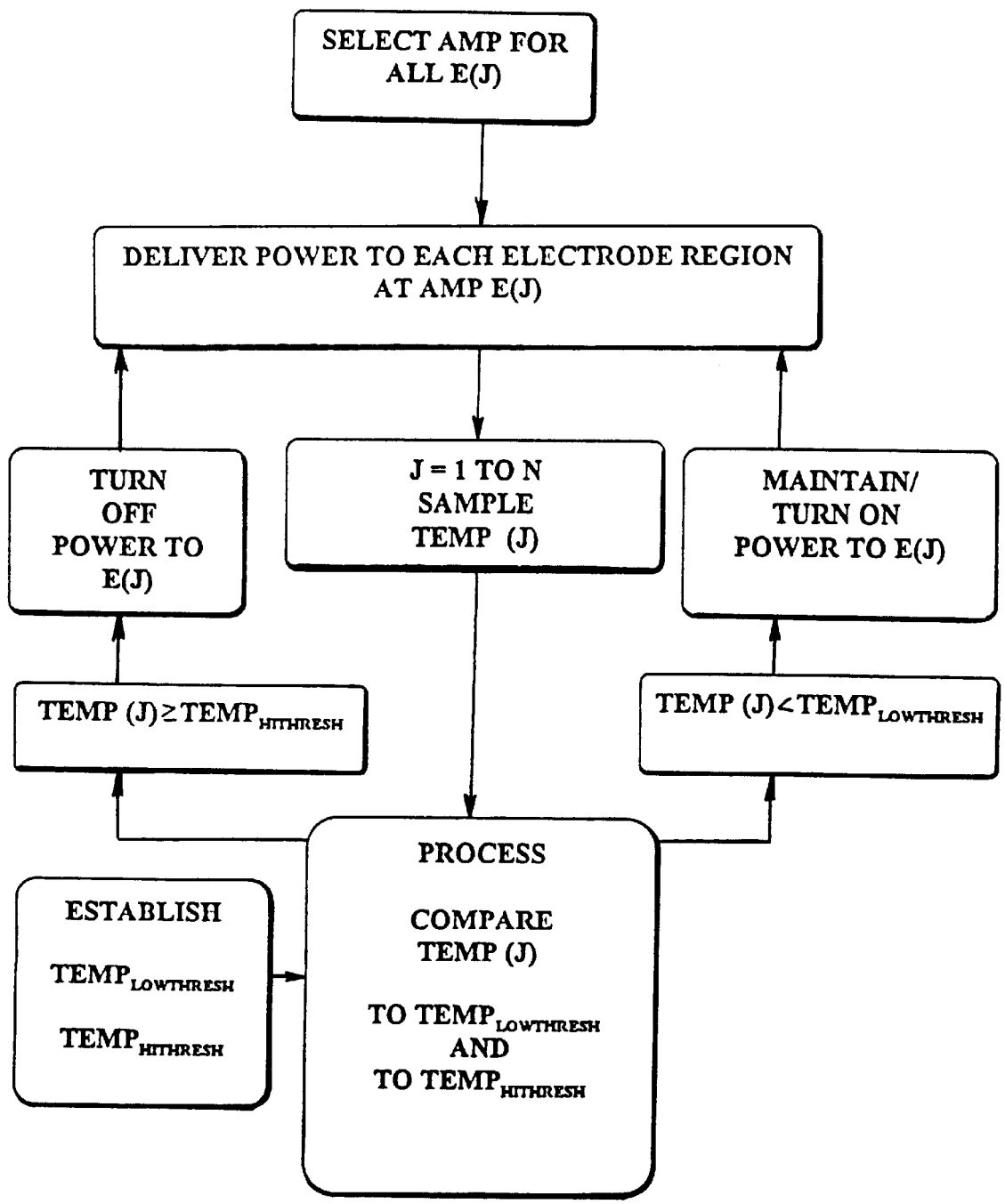
FIG. 23 is a schematic flow chart showing an implementation of the temperature feedback controller shown in FIGS. 19 and 20, using temperature control with hysteresis.

In this mode (see FIG. 23), as in the previous modes, the system 200 cycles in successive data acquisition periods to sequentially register the temperature sensed by the sensing elements TEMP(J) for the electrode regions E(J). As before, when there are multiple sensing elements associated with each electrode region, the system 200 registers all sensed temperatures for the particular electrode region and selects among these the highest sensed temperature, which becomes TEMP(J).

In this mode, the microcontroller 231 compares the temperature sensed locally at each electrode region TEMP(J) during each data acquisition period to high and low threshold temperatures TEMP$_{HITHRESH}$ and TEMP$_{LOWTHRESH}$, where

TEMP$_{HITHRESH}$-TEMP$_{SET}$+INCR where

TEMP$_{LOWTHRESH}$-TEMP$_{SET}$-INCR

TEMP$_{SET}$ is the set point temperature, and INCR is a preselected increment.

When operated in this mode, the microcontroller 231 operates the power switch interface 230 to turn a given electrode region E(J) off when the local temperature sensed at that electrode region TEMP (J)≧TEMP$_{HITHRESH}$. The microcontroller 231 keeps the electrode region turned off until the locally sensed temperature TEMP(J) drops below TEMP$_{LOWTHRESH}$. The microcontroller 231 turns a given electrode region E(J) on and supplies power at a selected voltage amplitude when the local temperature sensed at that electrode region TEMP(J)<TEMP$_{LOWTHRESH}$.

The values for TEMP$_{SET}$ and INCR can vary according to the judgment of the physician and empirical data. As before stated, a representative value for TEMP$_{SET}$ is believed to lie in the range of 40° C. and 95° C., with a preferred value of 70° C. A representative value of INCR is believed to lie in the range of 2° C. to 8° C., with a preferred representative value of around 5° C.

In this implementation, the controller 215 establishes a constant RF voltage amplitude sufficiently high to maintain the desired temperature conditions during hysteresis. Alternatively, the controller 215 can have the capability to adjust voltage should the coolest sensed temperature TEMP$_{SMIN}$ decrease below a selected lower limit below TEMP$_{LOWTHRESH}$, or should the longest duty cycle exceed a predetermined value. It should be appreciated that there are other ways of adjusting and maintaining the amplitude while the hysteresis control method is carried out.

Differential Temperature Disabling

In this mode (see FIG. 24), the temperature controller 215 selects at the end of each data acquisition phase the sensed temperature that is the greatest for that phase (TEMP$_{SMAX}$). The temperature controller 215 also selects for that phase the sensed temperature that is the lowest (TEMP$_{SMIN}$).

The controller 215 compares the selected hottest sensed temperature TEMP$_{SMAX}$ to a selected high set point temperature TEMP$_{HISET}$. The comparison generates a control signal that collectively adjusts the amplitude of the RF voltage for all electrodes using proportional, PID, or fuzzy logic control techniques.

In a proportion control implementation scheme:

(i) If TEMP$_{SMAX}$>TEMP$_{HISET}$, the control signal collectively decreases the amplitude of the RF voltage delivered to all electrode regions;

(ii) If TEMP$_{SMAX}$<TEMP$_{HISET}$, the control signal collectively increases the amplitude of the RF voltage delivered to all electrode regions:

(iii) If TEMP$_{SMAX}$=TEMP$_{HISET}$, no change in the amplitude of the RF voltage delivered to all electrode regions is made.

It should be appreciated that the temperature controller 215 can select for amplitude control purposes any one of the sensed temperatures TEMP$_{SMAX}$, TEMP$_{SMIN}$, or temperatures in between, and compare this temperature condition to a preselected temperature condition.

Working in tandem with the amplitude control function of the temperature controller 215, the microcontroller 231 governs the delivery of power to the electrode regions based upon difference between a given local temperature TEMP(J) and TEMP$_{SMIN}$. This implementation computes the difference between local sensed temperature TEMP(J) and TEMP$_{SMIN}$ and compares this difference to a selected set point temperature difference ΔTEMP$_{SET}$. The comparison generates a control signal that governs the delivery of power to the electrode regions.

If the local sensed temperature TEMP(J) for a given electrode region E(J) exceeds the lowest sensed temperature TEMP$_{SMIN}$ by as much as or more than ΔTEMP$_{SET}$ (that is, if TEMP(J)−TEMP$_{SMIN}$≧ΔTEMP$_{SET}$), the microcontroller 231 turns the given electrode region E(J) off. The microcontroller 231 turns the given electrode E(J) back on when TEMP(J)−TEMP$_{SMIN}$<ΔTEMP$_{SET}$.

Figure 25:
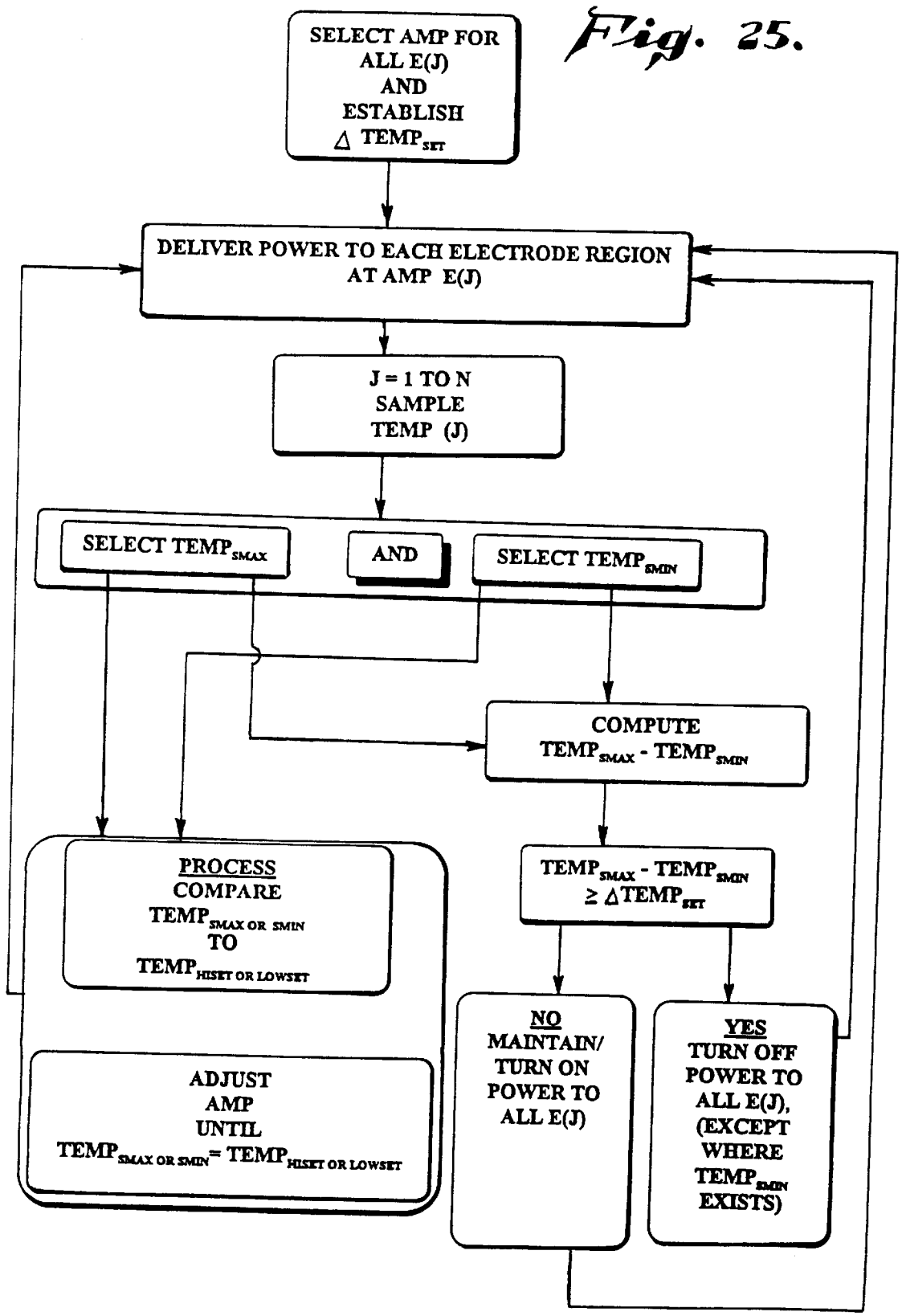
FIG. 25 is a schematic flow chart showing an implementation of the temperature feedback controller shown in FIGS. 19 and 20, using differential temperature disabling.

Alternatively (see FIG. 25), instead of comparing TEMP (J) and TEMP$_{SMIN}$, the microcontroller 231 can compare TEMP$_{SMAX}$ and TEMP$_{SMIN}$. When the difference between TEMP$_{SMAX}$ and TEMP$_{SMIN}$ equals or exceeds a predetermined amount ΔTEMP$_{SET}$, the controller 231 turns all electrode regions off, except the electrode region where TEMP$_{SMIN}$ exists. The controller 231 turns these electrode regions back on when the temperature difference between TEMP$_{SMAX}$ and TEMP$_{SMIN}$ is less than ΔTEMP$_{SET}$.

Some of the above-described temperature-based control schemes alter power by adjusting the amplitude of the RF voltage. It should be appreciated that, alternatively, power can be altered by the adjusting the amplitude of RF current. Therefore, the quantity AMP$_{E(J)}$ used in this Specification can mean either RF voltage amplitude or RF current amplitude.

III. Selecting Among Multiple Temperature Sensing Elements

As previously described, a given electrode region can have more than one temperature sensing element associated with it. In the previously descibed ablation control modes, the controller 215 registers all sensed temperatures for the given electrode region and selects among these the highest sensed temperature, which constitutes TEMP(J). There are alternative ways of making this selection.

Deriving Predicted Hottest Temperature

Because of the heat exchange between the tissue and the electrode region, the temperature sensing elements may not measure exactly the maximum temperature at the region. This is because the region of hottest temperature occurs beneath the surface of the tissue at a depth of about 0.5 to 2.0 mm from where the energy emitting electrode region (and the associated sensing element) contacts the tissue. If the power is applied to heat the tissue too quickly, the actual maximum tissue temperature in this subsurface region may exceed 100° C. and lead to tissue desiccation.

Figure 26:
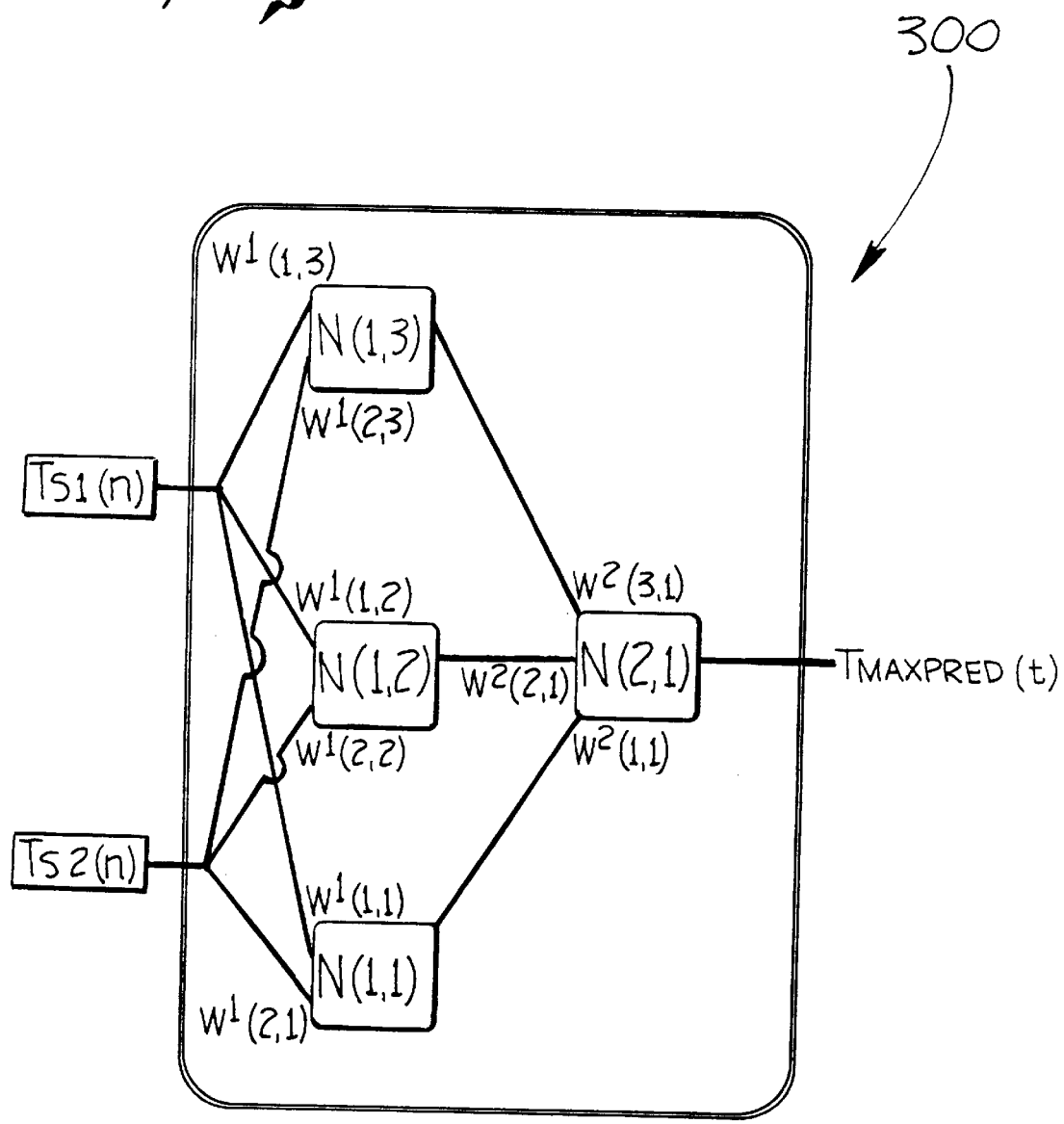
FIG. 26 is a schematic view of a neural network predictor, which receives as input the temperatures sensed by multiple sensing elements at a given electrode region and outputs a predicted temperature of the hottest tissue region.

FIG. 26 shows an implementation of a neural network predictor 300, which receives as input the temperatures sensed by multiple sensing elements S(J,K) at each electrode region, where J represents a given electrode region (J=1 to N) and K represents the number of temperature sensing elements on each electrode region (K=1 to M). The predictor 300 outputs a predicted temperature of the hottest tissue region $T_{MAXPRED(t)}$. The controller 215 and microcontroller 231 derive the amplitude and duty cycle control signals based upon $T_{MAXPRED(t)}$, in the same manners already described using TEMP(J).

The predictor 300 uses a two-layer neural network, although more hidden layers could be used. As shown in FIG. 26, the predictor 300 includes a first and second hidden layers and four neurons, designated $N_{(L,X)}$, where L identifies the layer 1 or 2 and X identifies a neuron on that layer. The first layer (L=1) has three neurons (X=1 to 3), as follows $N_{(1,1)}$; $N_{(1,2)}$; and $N_{(1,3)}$. The second layer (L=2) comprising one output neuron (X=1), designated $N_{(2,1)}$.

Temperature readings from the multiple sensing elements, only two of which—TS1(n) and TS2(n)—are shown for purposes of illustration, are weighed and inputted to each neuron $N_{(1,1)}$; $N_{(1,2)}$; and $N_{(1,3)}$ of the first layer. FIG. 26 represents the weights as $W^L_{(k,N)}$, where L=1; k is the input sensor order; and N is the input neuron number 1, 2, or 3 of the first layer.

The output neuron $N_{(2,1)}$ of the second layer receives as inputs the weighted outputs of the neurons $N_{(1,1)}$; $N_{(1,2)}$; and $N_{(1,3)}$. FIG. 26 represents the output weights as $W^L_{(O,X)}$, where L=2; O is the output neuron 1, 2, or 3 of the first layer; and X is the input neuron number of the second layer. Based upon these weighted inputs, the output neuron $N_{(2,1)}$ predicts $T_{MAXPRED(t)}$.

The predictor 300 must be trained on a known set of data containing the temperature of the sensing elements TS1 and TS2 and the temperature of the hottest region, which have been previously acquired experimentally. For example, using a back-propagation model, the predictor 300 can be trained to predict the known hottest temperature of the data set with the least mean square error. Once the training phase is completed, the predictor 300 can be used to predict $T_{MAXPRED(t)}$.

Other types of data processing techniques can be used to derive $T_{MAXPRED(t)}$. See, e.g., copending patent application Ser. No. 08/266,934, filed Jun. 27, 1994, and entitled "Tissue Heating and Ablation Systems and Methods Using Predicted Temperature for Monitoring and Control."

The illustrated and preferred embodiments use digital processing controlled by a computer to analyze information and generate feedback signals. It should be appreciated that other logic control circuits using micro-switches, AND/OR gates, invertors, anolog circuits, and the like are equivalent to the micro-processor controlled techniques shown in the preferred embodiments.

Various features of the invention are set forth in the following claims.

We claim:

1. A system for ablating body tissue including multiple emitters of ablating energy supported adjacent body tissue by at least one supporting structure comprising at least one temperature sensing element supported in proximity with each energy emitter for measuring temperature at the emitter, a power controller coupled to a source of ablating energy and to each energy emitter to convey ablating energy individually from the source to each emitter in a sequence of power pulses, each power pulse having a duty cycle and an amplitude, wherein power delivered to each emitter for ablating tissue is expressed as follows:

$$POWER \sim AMPLITUDE^2 \times DUTYCYCLE$$

a processing element coupled to each temperature sensing element for periodically reading the temperature measured by each temperature sensing element and comparing the temperature to a desired temperature established for all emitters to generate a signal individually for each emitter based upon the comparison, and a temperature controller coupled to the power controller and the processing element for causing the power controller to individually vary the power pulse to each emitter based upon the signal for that emitter to maintain the temperatures at all emitters essentially at the desired temperature during tissue ablation.

2. A system according to claim 1 wherein the temperature controller includes means for causing the power controller to vary the power pulse by individually varying the amplitude of the power pulse based upon the signal for that emitter, while maintaining the duty cycle of the power pulses essentially the same for all emitters.

3. A system according to claim 2 wherein the means for causing the power controller to vary the power pulse by varying amplitude maintains the duty cycle at 1/N, where N is the number of energy emitters.

4. A system according to claim 2 wherein the the means for causing the power controller to vary the power pulse by varying amplitude varies amplitude by varying either voltage or current.

5. A system according to claim 2 wherein the the means for causing the power controller to vary the power pulse by varying amplitude individually turns off an energy emitter when the temperature measured at the emitter equals or exceeds the desired temperature by a predetermined amount and individually turns on the emitter when the temperature measured at the emitter is less than the desired temperature by a predetermined amount.

6. A system according to claim 1 wherein the temperature controller includes means for causing the power controller to vary the power pulse by individually varying the duty cycle of the emitter based upon the signal for that emitter, while maintaining the amplitude of the power pulses essentially the same for all emitters.

7. A system according to claim 6 wherein the means for causing the power controller to vary the power pulse by varying duty cycle individually turns off an energy emitter when the temperature measured at the emitter equals or exceeds the desired temperature by a predetermined amount and individually turns on the emitter when the temperature measured at the emitter is less than the desired temperature by a predetermined amount.

8. A system according to claim 1
wherein the temperature controller includes means for causing the power controller to vary the power pulse by individually varying both the duty cycle and the amplitude of the power pulse for each energy emitter based upon the signal for that emitter.

9. A system according to claim 8
wherein the means for causing the power controller to vary the power pulse by varying both duty cycle and amplitude individually turns off an energy emitter when the temperature measured at the emitter equals or exceeds the desired temperature by a predetermined amount and individually turns on the emitter when the temperature measured at the emitter is less than the desired temperature by a predetermined amount.

10. A system according to claim 8
wherein the means for causing the power controller to vary the power pulse by varying both duty cycle and amplitude varies amplitude by varying either voltage or current.

11. A tissue ablation system comprising
an ablating element comprising at least one structure supporting at least two zones for emitting ablating energy E(J), where J=2 to N, N being the total number of zones,
at least one temperature sensing element supported in proximity with each zone E(J) for measuring a temperature condition localized with respect to the zone E(J), the localized temperature condition being designated TEMP(J),
a power controller coupled to a source of ablating energy and to the zones E(J) including a switching element to convey ablating energy individually to each zone E(J) in a power pulse having a duty cycle $DUTYCYCLE_{E(J)}$ and an amplitude $AMP_{E(J)}$, $DUTYCYCLE_{E(J)}$ being set to be essentially the same for all E(J), wherein the power $P_{E(J)}$ delivered to each zone E(J) is expressed as follows:

$$P_{E(J)} \sim AMP_{E(J)}^2 \times DUTYCYCLE_{E(J)}$$

a processing element coupled to the at least one temperature sensing element including
means for periodically reading the temperature condition measured by each temperature sensing element TEMP(J),
means for comparing the read temperature condition TEMP(J) to a desired temperature condition $TEMP_{SET}$ to generate a signal SIGNAL(J) based upon the comparison, and
a temperature controller coupled to the power controller and the processing element including control means for causing the power controller to vary the power pulse to each zone E(J) based upon SIGNAL(J) by varying $AMP_{E(J)}$ while keeping $DUTYCYCLE_{E(J)}$ essentially the same for all E(J), to maintain TEMP(J)≈$TEMP_{SET}$ for all E(J).

12. A system according to claim 11
wherein the control means keeps $DUTYCYCLE_{E(J)}$ set at 1/N for all E(J).

13. A system according to claim 11
wherein the control means varies AMPE(J) by varying either voltage or current.

14. A tissue ablation system comprising
an ablating element comprising at least one structure supporting at least two zones for emitting ablating energy E(J), where J=2 to N, N being the total number of zones,
at least one temperature sensing element supported in proximity with each zone E(J) for measuring a temperature condition localized with respect to the zone E(J), the localized temperature condition being designated TEMP(J),
a power controller coupled to a source of ablating energy and to the zones E(J) including a switching element to convey ablating energy individually to each zone E(J) in a power pulse having a duty cycle $DUTYCYCLE_{E(J)}$ and an amplitude $AMP_{E(J)}$, $AMP_{E(J)}$ being set to be essentially the same for all E(J), wherein the power $P_{E(J)}$ delivered to each zone E(J) is expressed as follows:

$$P_{E(J)} \sim AMP_{E(J)}^2 \times DUTYCYCLE_{E(J)}$$

a processing element coupled to the at least one temperature sensing element including
means for periodically reading the temperature condition measured by each temperature sensing element TEMP(J),
means for comparing the read temperature condition TEMP(J) to a desired temperature condition $TEMP_{SET}$ to generate a signal SIGNAL(J) based upon the comparison, and
a temperature controller coupled to the power controller and the processing element including control means for causing the power controller to vary the power pulse to each zone E(J) based upon SIGNAL(J) by varying $DUTYCYCLE_{E(J)}$ while keeping $AMP_{E(J)}$ essentially the same for all E(J), to maintain TEMP(J)≈$TEMP_{SET}$ for all E(J).

15. A tissue ablation system comprising
an ablating element comprising at least one structure supporting at least two zones for emitting ablating energy E(J), where J=2 to N, N being the total number of zones,
at least one temperature sensing element supported in proximity with each zone E(J) for measuring a temperature condition localized with respect to the zone E(J), the localized temperature condition being designated TEMP(J),
a power controller coupled to a source of ablating energy and to the zones E(J) including a switching element to convey ablating energy individually to each zone E(J) in a power pulse having a duty cycle $DUTYCYCLE_{E(J)}$ and an amplitude $AMP_{E(J)}$, $AMP_{E(J)}$ being set to be essentially the same for all E(J), wherein the power $P_{E(J)}$ delivered to each zone E(J) is expressed as follows:

$$P_{E(J)} \sim AMP_{E(J)}^2 \times DUTYCYCLE_{E(J)}$$

a processing element coupled to the at least one temperature sensing element including
means for periodically reading the temperature condition measured by each temperature sensing element TEMP(J), means for identifying the lowest read temperature condition $TEMP_{SMIN}$ of all TEMP(J), and means for comparing the lowest read temperature condition $TEMP_{SMIN}$ to a desired temperature condition $TEMP_{SET}$ to generate a signal based upon the comparison, and a temperature controller coupled to the power controller and to the processing element including control means for causing the power controller to vary the power pulse to each zone E(J) based upon the signal by varying $AMP_{E(J)}$ for all E(J) to maintain $TEMP_{SMIN} \approx TEMP_{SET}$.

16. A tissue ablation system comprising an ablating element comprising at least one structure supporting at least two zones for emitting ablating energy E(J), where J=2 to N, N being the total number of zones, at least one temperature sensing element supported in proximity with each zone E(J) for measuring a temperature condition localized with respect to the zone E(J), the localized temperature condition being designated TEMP(J), a power controller coupled to a source of ablating energy and to the zones E(J) including a switching element to convey ablating energy individually to each zone E(J) in a power pulse having a duty cycle $DUTYCYCLE_{E(J)}$ and an amplitude $AMP_{E(J)}$, $AMP_{E(J)}$ being set to be essentially the same for all E(J), wherein the power $P_{E(J)}$ delivered to each zone E(J) is expressed as follows:

$$P_{E(J)} \sim AMP_{E(J)}^2 \times DUTYCYCLE_{E(J)}$$

a processing element coupled to the at least one temperature sensing element including means for periodically reading the temperature condition measured by each temperature sensing element TEMP(J), means for identifying the lowest read temperature condition $TEMP_{SMIN}$ of all TEMP(J), and means for comparing the lowest read temperature condition $TEMP_{SMIN}$ to a desired temperature condition $TEMP_{SET}$ to generate a signal based upon the comparison, and a temperature controller coupled to the power controller and to the processing element including control means for causing the power controller to vary the power pulse to each zone E(J) based upon the signal by varying $AMP_{E(J)}$ for all E(J) to maintain $TEMP_{SMIN} \approx TEMP_{SET}$ while also varying the $DUTYCYCLE_{E(J)}$ of each zone E(J) where TEMP(J) >$TEMP_{SMIN}$ to maintain TEMP(J)$\approx TEMP_{SET}$ for each such zone.

17. A system according to claim 14 or 15 or 16 wherein the control means varies $AMP_{E(J)}$ by varying either voltage or current.

18. A system for ablating body tissue including multiple emitters of ablating energy supported adjacent body tissue by at least one supporting structure comprising at least one temperature sensing element supported in proximity with each energy emitter for measuring temperature at the emitter, a power controller coupled to a source of ablating energy and to each energy emitter to convey ablating energy to the emitters, a processing element coupled to the at least one temperature sensing element for periodically reading the temperature measured by each temperature sensing element and selecting one of the measured temperatures based upon preestablished criteria for comparison to a desired temperature to generate a signal, and a temperature controller coupled to the power controller and to the processing element for causing the power controller to convey ablating energy to the emitters based upon the signal.

19. A system according to claim 18 wherein the processing element includes means for selecting the highest one of the measured temperatures.

20. A system for ablating body tissue including multiple emitters of ablating energy supported adjacent body tissue by at least one supporting structure comprising at least one temperature sensing element supported in proximity with each energy emitter for measuring temperature at the emitter, a power controller coupled to a source of ablating energy and to each energy emitter to convey ablating energy individually to each emitter in a sequence of power pulses, each power pulse having a duty cycle and an amplitude, wherein ablating power delivered to each emitter is expressed as follows:

$$POWER \sim AMPLITUDE^2 \times DUTYCYCLE$$

a processing element coupled to the at least one temperature sensing element for periodically reading the temperature measured by each temperature sensing element and selecting one of the measured temperatures based upon preestablished criteria for comparison to a desired temperature to generate a signal, and a temperature controller coupled to the power controller and to the processing element for causing the power controller to vary the power pulses to the emitters based upon the signal.

21. A system according to claim 20 wherein the processing element includes means for selecting the highest one of the measured temperature.

22. A system according to claim 20 wherein the temperature controller includes means for causing the power controller to vary the power pulses by varying the amplitudes of the power pulses for all emitters based upon the signal to maintain the amplitudes of the power pulses essentially the same for all emitters.

23. A system according to claim 20 wherein the means for causing the power controller to vary the power pulses by varying amplitudes varies amplitudes by varying either voltage or current.

24. A system for ablating body tissue including multiple emitters of ablating energy supported adjacent body tissue by at least one supporting structure comprising at least one temperature sensing element supported in proximity with each energy emitter for measuring temperature at the emitter, a power controller coupled to a source of ablating energy and to each energy emitter to convey ablating energy individually to each emitter, a processing element coupled to the at least one temperature sensing element for periodically reading the temperature measured by each temperature sensing element and selecting one of the measured temperatures based upon preestablished criteria and for comparing the temperature measured by each temperature sensor to the selected one of the measured temperatures to generate a signal individually for each emitter based upon the comparison, and a temperature controller coupled to the power controller and to the processing element for causing the power controller to individually control the conveyance of ablating energy to each emitter based upon the signal for that emitter.

25. A system according to claim 24
wherein the temperature controller includes means for causing the power controller to individually turn off and turn on an energy emitter based upon the signal for that emitter.

26. A system according to claim 24
wherein the the processing element includes means for selecting the lowest one of the measured temperatures.

27. A system according to claim 24
wherein the processing element includes means for deriving a difference between the temperature measured by each temperature sensor and the selected one of the measured temperatures and compares the difference to a predetermined value to generate the signal.

28. A system according to claim 27
wherein the temperature controller includes means for causing the power controller to individually turn off an energy emitter when the difference for that emitter equals or exceeds the predetermined value and individually turn on the emitter when the difference for that emitter is less than the predetermined value.

29. A tissue ablation system comprising
an ablating element comprising at least one structure supporting at least two zones for emitting ablating energy E(J), where J=2 to N, N being the total number of zones, at least one temperature sensing element supported in proximity with each zone E(J) for measuring a temperature condition localized with respect to the zone E(J), the localized temperature condition being designated TEMP(J), a power controller coupled to a source of ablating energy and to the zones E(J) including a switching element to convey ablating energy individually to each zone E(J) in a power pulse having a duty cycle $DUTYCYCLE_{E(J)}$ and an amplitude $AMP_{E(J)}$, wherein the power $P_{E(J)}$ delivered to each zone E(J) is expressed as follows:

$$P_{E(J)} \sim AMP_{E(J)}^2 \times DUTYCYCLE_{E(J)}$$

a processing element coupled to the at least one temperature sensing element including
means for periodically reading the temperature condition measured by each temperature sensing element TEMP(J),
means for comparing each read temperature condition TEMP(J) to a prescribed low threshold temperature condition $TEMP_{LOWTHRESH}$ and a prescribed high threshold temperature condition $TEMP_{HITHRESH}$, and a temperature controller coupled to the power controller and to the processing element for causing the power controller to turn off a given zone E(J) when TEMP(J) for that zone $\geq TEMP_{HITHRESH}$ and for turn on the given zone E(J) when TEMP(J) for that zone $< TEMP_{LOWTHRESH}$.

30. A system according to claim 29
wherein the power controller includes means for establishing and maintaining essentially the same $AMP_{E(J)}$ for all E(J) during operation of the temperature controller.

31. A system according to claim 29
wherein the temperature controller includes means for causing the power controller to adjust $AMP_{E(J)}$ for at least one zone E(J) according to prescribed criteria.

32. A system according to claim 29
wherein the processing element further includes
means for identifying the lowest read temperature condition $TEMP_{SMIN}$ of all TEMP(J), and
means for comparing the lowest read temperature condition $TEMP_{SMIN}$ to a prescribed low temperature condition $TEMP_{LOW}$ to generate a signal based upon the comparison, and wherein the temperature controller includes means for causing the power controller to adjust $AMP_{E(J)}$ based upon the signal to maintain $TEMP_{SMIN}$ above $TEMP_{LOW}$.

33. A system according to claim 29
wherein the temperature controller includes means for causing the power controller to adjust $DUTYCYCLE_{E(J)}$ for at least one zone E(J) based upon prescribed criteria.

34. A system for ablating body tissue comprising
an emitter of ablating energy supported on a structure,
at least two temperature sensing elements supported in proximity with the energy emitter for measuring temperatures at the emitter,
a power controller coupled to a source of ablating energy and to the energy emitter to convey ablating energy to the emitter,
a processing element coupled to the at least two temperature sensing elements for periodically reading the temperature measured by each temperature sensing element and selecting the hottest one of the measured temperatures and for comparing the selected hottest temperature to a desired temperature to generate a signal based upon the comparison, and
a temperature controller coupled to the power controller and to the processing element for causing the power controller to convey energy to the emitter based upon the signal.

35. A system for ablating body tissue comprising
an emitter of ablating energy supported on a structure,
at least two temperature sensing elements supported in proximity with the energy emitter for measuring temperatures at the emitter,
a power controller coupled to a source of ablating energy and to the energy emitter to convey ablating energy to the emitter,
a processing element coupled to the at least two temperature sensing elements for periodically reading the temperature measured by each temperature sensing element and deriving therefrom a prediction of the hottest tissue temperature at the emitter and for comparing the predicted hottest temperature to a desired temperature to generate a signal based upon the comparison, and
a temperature controller coupled to the power controller and to the processing element for causing the power controller to convey energy to the emitter based upon the signal.

36. A system for ablating body tissue including multiple emitters of ablating energy supported adjacent body tissue by at least one supporting structure comprising

- at least two temperature sensing elements supported in proximity with each energy emitter for measuring temperatures at the emitter,
- a power controller coupled to a source of ablating energy and to each energy emitter to convey ablating energy individually to each emitter,
- a processing element coupled to the at least two temperature sensing elements for periodically reading the temperatures measured by the temperature sensing elements for each emitter and selecting for each emitter the hottest one of the measured temperatures and for comparing the hottest one of the temperatures for each emitter to a desired temperature established for all emitters to generate a signal individually for each emitter based upon the comparison, and
- a temperature controller coupled to the power controller and to the processing element for causing the power controller to individually convey energy to each emitter based upon the signal for that emitter to maintain the hottest temperature at all emitters essentially at the desired temperature during tissue ablation.

37. A system for ablating body tissue including multiple emitters of ablating energy supported adjacent body tissue by at least one supporting structure comprising

- at least two temperature sensing elements supported in proximity with each energy emitter for measuring temperatures at the emitter,
- a power controller coupled to a source of ablating energy and to each energy emitter to convey ablating energy individually to each emitter in a sequence of power pulses, each power pulse having a duty cycle and an amplitude, wherein power delivered to each emitter for ablating tissue is expressed as follows:

$$POWER \sim AMPLITUDE^2 \times DUTYCYCLE$$

- a processing element coupled to the at least two temperature sensing elements for periodically reading the temperatures measured by the temperature sensing elements for each emitter and selecting for each emitter the hottest one of the measured temperatures and for comparing the hottest one of the temperatures for each emitter to a desired temperature established for all emitters to generate a signal individually for each emitter based upon the comparison, and
- a temperature controller coupled to the power controller and to the processing element for causing the power controller to individually vary the power pulse to each emitter based upon the signal for that emitter to maintain the hottest temperature at all emitters essentially at the desired temperature during tissue ablation.

38. A system for ablating body tissue including multiple emitters of ablating energy supported adjacent body tissue by at least one supporting structure comprising

- at least two temperature sensing elements supported in proximity with each energy emitter for measuring temperatures at the emitter,
- a power controller coupled to a source of ablating energy and to each energy emitter to convey ablating energy individually to each emitter in a sequence of power pulses, each power pulse having a duty cycle and an amplitude, wherein power delivered to each emitter for ablating tissue is expressed as follows:

$$POWER \sim AMPLITUDE^2 \times DUTYCYCLE$$

- a processing element coupled to the at least two temperature sensing elements for periodically reading the temperatures measured by the temperature sensing elements for each emitter and predicting for each emitter the hottest tissue temperature and for comparing the predicted hottest temperature for each emitter to a desired temperature established for all emitters to generate a signal individually for each emitter based upon the comparison, and
- a temperature controller coupled to the power controller and to the processing element for causing the power controller to individually vary the power pulse to each emitter based upon the signal for that emitter to maintain the predicted hottest temperature at all emitters essentially at the desired temperature during tissue ablation.

39. A method for ablating body tissue using multiple emitters of ablating energy comprising the steps of conveying ablating energy individually to each emitter in a sequence of power pulses, each power pulse having a duty cycle and an amplitude, wherein power delivered to each emitter for ablating tissue is expressed as follows:

$$POWER \sim AMPLITUDE^2 \times DUTY\ CYCLE$$

periodically sensing temperature at each emitter, comparing the sensed temperatures to a desired temperature established for all emitters to generate a signal individually for each emitter based upon the comparison, and individually varying the power pulse to each emitter based upon the signal for that emitter to maintain the temperatures at all emitters essentially at the desired temperature during tissue ablation.

40. A method according to claim 39 wherein the pulse power varying step includes individually varying the amplitude of the power pulse based upon the signal for that emitter, while maintaining the duty cycle of the power pulses essentially the same for all emitters.

41. A method according to claim 39 wherein the pulse power varying step includes individually varying the duty cycle of the emitter based upon the signal for that emitter, while maintaining the amplitude of the power pulses essentially the same for all emitters.

42. A method according to claim 39 wherein the pulse power varying step includes individually varying both the duty cycle and the amplitude of the power pulse for each energy emitter based upon the signal for that emitter.

43. A method according to claim 39 and further including the step of individually turning off an energy emitter when the temperature measured at the emitter equals or exceeds a predetermined amount and individually turning on the emitter when the temperature measured at the emitter is less than the predetermined amount.

44. A method for ablating body tissue using multiple emitters of ablating energy comprising the steps of conveying ablating energy to the emitters, periodically sensing temperature at each emitter, selecting one of the sensed temperatures based upon preestablished criteria for comparison to a desired temperature to generate a signal, and controlling the conveyance of ablating energy to all emitters based upon the signal.

45. A method according to claim 44 wherein the selecting step selects the highest one of the sensed temperatures.

46. A method according to claim 44 wherein the selecting step selects for each emitter a prediction of the hottest tissue temperature based upon the sensed temperatures at that emitter.

47. A method for ablating body tissue using multiple emitters of ablating energy comprising the steps of conveying ablating energy individually to each emitter, periodically sensing temperature at each emitter, selecting one of the sensed temperatures based upon preestablished criteria, comparing the sensed temperature at each emitter to the selected one of the sensed temperatures to generate a signal individually for each emitter based upon the comparison, and individually controlling the conveyance of ablating energy to each emitter based upon the signal for that emitter.

48. A method according to claim 47 wherein the controlling step includes the step of individually turning off and turning on an energy emitter based upon the signal for that emitter.

49. A method according to claim 47 wherein the selecting step selects the lowest one of the sensed temperatures.

50. A method for ablating body tissue comprising the steps of conveying ablating energy to an emitter, periodically sensing at least two temperatures at the emitter, selecting the hottest one of the selected temperatures, comparing the selected hottest temperature to a desired temperature to generate a signal based upon the comparison, and controlling the conveyance of energy to the emitter based upon the signal.

51. A method for ablating body tissue comprising the steps of conveying ablating energy to an emitter, periodically sensing at least two temperatures at the emitter, predicting the hottest tissue temperature at the emitter based upon the sensed temperatures, comparing the predicted hottest tissue temperature to a desired temperature to generate a signal based upon the comparison, and controlling the conveyance of energy to the emitter based upon the signal.

52. A method ablating body tissue using multiple emitters of ablating energy comprising the steps of conveying ablating energy individually to each emitter, periodically sensing at least two temperatures at each emitter, selecting for each emitter the hottest one of the sensed temperatures, comparing the hottest one of the temperatures for each emitter to a desired temperature established for all emitters to generate a signal individually for each emitter based upon the comparison, and individually controlling the conveyance of energy to each emitter based upon the signal for that emitter to maintain the hottest temperature at all emitters essentially at the desired temperature during tissue ablation.

53. A method ablating body tissue using multiple emitters of ablating energy comprising the steps of conveying ablating energy individually to each emitter, periodically sensing at least two temperatures at each emitter, predicting the hottest tissue temperature at each emitter based upon temperatures sensed at that emitter, comparing the predicted hottest tissue temperature for each emitter to a desired temperature established for all emitters to generate a signal individually for each emitter based upon the comparison, and individually controlling the conveyance of energy to each emitter based upon the signal for that emitter to maintain the predicted hottest tissue temperature at all emitters essentially at the desired temperature during tissue ablation.

54. A system for ablating body tissue including multiple emitters of ablating energy supported adjacent body tissue by at least one supporting structure comprising at least one temperature sensing element supported in proximity with each energy emitter for measuring temperature at the emitter, a power controller coupled to a source of ablating energy and to each energy emitter to convey ablating energy individually from the source to each emitter in a sequence of power pulses, each power pulse having a duty cycle and an amplitude, wherein power delivered to each emitter for ablating tissue is expressed as follows:

$$POWER \sim AMPLITUDE^2 \times DUTYCYCLE$$

an element coupled to each temperature sensing element and to the power controller to vary the power pulses conveyed by the power controller including means for periodically sensing temperature at each emitter using the at least one temperature sensing element, means for comparing the sensed temperatures to a desired temperature established for all emitters to generate a signal individually for each emitter based upon the comparison, and means for causing the power controller to individually vary the power pulse to each emitter based upon the signal for that emitter to maintain the temperatures at all emitters essentially at the desired temperature during tissue ablation.

55. A system according to claim 54 wherein the element includes means for individually varying the amplitude of the power pulse based upon the signal for that emitter, while maintaining the duty cycle of the power pulses essentially the same for all emitters.

56. A system according to claim 54 wherein the element includes means for individually varying the duty cycle of the emitter based upon the signal for that emitter, while maintaining the amplitude of the power pulses essentially the same for all emitters.

57. A system according to claim 54
wherein the element includes means for individually varying both the duty cycle and the amplitude of the power pulse for each energy emitter based upon the signal for that emitter.

58. A system according to claim 54
wherein the element includes means for individually turning off an energy emitter when the temperature measured at the emitter equals or exceeds a predetermined amount and individually turning on the emitter when the temperature measured at the emitter is less than the predetermined amount.

59. A system for ablating body tissue including multiple emitters of ablating energy supported adjacent body tissue by at least one supporting structure comprising
  at least one temperature sensing element supported in proximity with each energy emitter for measuring temperature at the emitter,
  a power controller coupled to a source of ablating energy and to each energy emitter to convey ablating energy to the emitters, and
  an element coupled to each temperature sensing element and to the power controller to control the conveyance of ablating energy to the emitters including
    means for periodically sensing temperature at each emitter using the at least one temperature sensing element,
    means for selecting one of the sensed temperatures based upon preestablished criteria for comparison to a desired temperature to generate a signal, and
    means for causing the power controller to convey ablating energy to all emitters based upon the signal.

60. A system according to claim 59
wherein the means for selecting one of the sensed temperatures comprises means for selecting the highest one of the sensed temperatures.

61. A system according to claim 59
wherein the means for selecting one of the sensed temperatures comprises means for selecting for each emitter a prediction of the hottest tissue temperature based upon the sensed temperatures at that emitter.

62. A system for ablating body tissue including multiple emitters of ablating energy supported adjacent body tissue by at least one supporting structure comprising
  at least one temperature sensing element supported in proximity with each energy emitter for measuring temperature at the emitter,
  a power controller coupled to a source of ablating energy and to each energy emitter to convey ablating energy to the emitters, and
  an element coupled to each temperature sensing element and to the power controller to control the conveyance of ablating energy to the emitters including
    means for periodically sensing temperature at each emitter using the at least one temperature sensing element,
    means for selecting one of the sensed temperatures based upon preestablished criteria,
    means for comparing the sensed temperature at each emitter to the selected one of the sensed temperatures to generate a signal individually for each emitter based upon the comparison, and
    means for causing the power controller to individually control the conveyance of ablating energy to each emitter based upon the signal for that emitter.

63. A system according to claim 62
wherein the means for causing the power controller to individually control the conveyance of ablating energy comprises means for individually turning off and turning on an energy emitter based upon the signal for that emitter.

64. A system according to claim 62
wherein the means for selecting one of the sensed temperatures comprises means for selecting the lowest one of the sensed temperatures.

65. A system for ablating body tissue including multiple emitters of ablating energy supported adjacent body tissue by at least one supporting structure comprising
  at least two temperature sensing elements supported in proximity with each energy emitter for measuring temperature at the emitter,
  a power controller coupled to a source of ablating energy and to each energy emitter to convey ablating energy to the emitters, and
  an element coupled to each temperature sensing element and to the power controller to control the conveyance of ablating energy to the emitters including
    means for periodically sensing at least two temperatures at the emitter using the at least two temperature sensing elements,
    means for selecting the hottest one of the selected temperatures,
    means for comparing the selected hottest temperature to a desired temperature to generate a signal based upon the comparison, and
    means for causing the power controller to conveyance of energy to the emitter based upon the signal.

66. A system for ablating body tissue including multiple emitters of ablating energy supported adjacent body tissue by at least one supporting structure comprising
  at least two temperature sensing elements supported in proximity with each energy emitter for measuring temperature at the emitter,
  a power controller coupled to a source of ablating energy and to each energy emitter to convey ablating energy to the emitters, and
  an element coupled to each temperature sensing element and to the power controller to control the conveyance of ablating energy to the emitters including
    means for periodically sensing at least two temperatures at the emitter using the at least two temperature sensing elements,
    means for predicting the hottest tissue temperature at the emitter based upon the sensed temperatures,
    means for comparing the predicted hottest tissue temperature to a desired temperature to generate a signal based upon the comparison, and
    means for causing the power controller to convey energy to the emitter based upon the signal.

67. A system for ablating body tissue including multiple emitters of ablating energy supported adjacent body tissue by at least one supporting structure comprising
  at least two temperature sensing elements supported in proximity with each energy emitter for measuring temperature at the emitter,
  a power controller coupled to a source of ablating energy and to each energy emitter to convey ablating energy to the emitters, and
  an element coupled to each temperature sensing element and to the power controller to control the conveyance of ablating energy to the emitters including means for periodically sensing at least two temperatures at each emitter using the at least two temperature sensing elements, means for selecting for each emitter the hottest one of the sensed temperatures, means for comparing the hottest one of the temperatures for each emitter to a desired temperature established for all emitters to generate a signal individually for each emitter based upon the comparison, and means for causing the power controller to individually control the conveyance of energy to each emitter based upon the signal for that emitter to maintain the hottest temperature at all emitters essentially at the desired temperature during tissue ablation.

68. A system for ablating body tissue including multiple emitters of ablating energy supported adjacent body tissue by at least one supporting structure comprising at least two temperature sensing elements supported in proximity with each energy emitter for measuring temperature at the emitter, a power controller coupled to a source of ablating energy and to each energy emitter to convey ablating energy to the emitters, and an element coupled to each temperature sensing element and to the power controller to control the conveyance of ablating energy to the emitters including means for periodically sensing at least two temperatures at each emitter using the at least two temperature sensing elements, means for predicting the hottest tissue temperature at each emitter based upon temperatures sensed at that emitter, means for comparing the predicted hottest tissue temperature for each emitter to a desired temperature established for all emitters to generate a signal individually for each emitter based upon the comparison, and means for causing the power controller to individually control the conveyance of energy to each emitter based upon the signal for that emitter to maintain the predicted hottest tissue temperature at all emitters essentially at the desired temperature during tissue ablation.

* * * * *